US006943025B2

(12) United States Patent
Zon et al.

(10) Patent No.: US 6,943,025 B2
(45) Date of Patent: Sep. 13, 2005

(54) METHOD FOR IDENTIFYING GENES INVOLVED IN CELL PROLIFERATION

(75) Inventors: Leonard I. Zon, Wellesley, MA (US); James Amatruda, Cambridge, MA (US); Jennifer Shepard, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/758,007

(22) Filed: Jan. 10, 2001

(65) Prior Publication Data

US 2002/0137041 A1 Sep. 26, 2002

(51) Int. Cl.[7] .................. C12N 15/09; C12N 15/85; C12Q 1/68; C12Q 33/53; A01K 67/027
(52) U.S. Cl. .................. 435/440; 435/6; 435/7.1; 435/8; 800/8; 800/9; 800/10; 800/13; 800/20; 800/21; 800/22
(58) Field of Search .................. 800/8, 9, 10, 13, 800/20, 21, 22, 2; 435/440, 441, 455, 6, 7.1, 8

(56) References Cited

U.S. PATENT DOCUMENTS

| | | | | |
|---|---|---|---|---|
| 5,679,523 A | * | 10/1997 | Li et al. ................. | 435/6 |
| 5,756,476 A | * | 5/1998 | Epstein et al. ............ | 514/44 |
| 5,854,205 A | * | 12/1998 | O'Reilly et al. .......... | 514/2 |
| 5,932,418 A | | 8/1999 | Yager | |
| 6,015,670 A | | 1/2000 | Goodfellow | |
| 6,162,616 A | * | 12/2000 | Shyjan ................... | 435/69.1 |
| 6,511,818 B2 | * | 1/2003 | Vogelstein et al. ........ | 435/29 |

FOREIGN PATENT DOCUMENTS

| | | |
|---|---|---|
| WO | 99/42606 | 8/1999 |
| WO | 99/62333 | 12/1999 |
| WO | 99/67361 | 12/1999 |

OTHER PUBLICATIONS

Driever et al, J Clin Invest 1996;97:1788–94.*
Cheng et al, Biochem Cell Biol 1997;75:525–533.*
Alexander et al, Dev Genet 1998;22:288–299.*
Riley, B.B. et al., (1995) *PNAS*, 92: 5997–6001.
Brownlie, A. et al., (1998) *Nature Genetics*, 20: 244–250.
Kelly, P.D. et al., (2000) *Genome Research*, 10: 558–567.
Knapik, E.W. (2000) *Mammalian Genome*, 11: 511–519.
McClatchey, A., et al., *Curr Opin Genet Develop*, 8:304–310, 1998.
Eva A., *Semin Cell Bio*, 3:137–45, 1992.
Hrabe de Angelis M. et al., *Mutat Res*, 400:25–32, 1998.
Mechler B.M, et al., *EMBO J*, 4:1551–57, 1985.
Xu T., et al., *Development*, 121:1053–63, 1995.
St John, M.A., et al., *Nat Genet*, 21:182–186, 1999.
Couch, J., *Toxicol Pathol*, 24:602, 1996.
Spitsbergen J.M., et al., *Toxicol Pathol.* 28:716–25, 2000.
Khudoley, V.V., *Natl. Cancer Inst. Monogr*, 65:65–70, 1984.
Amanuma, K., et al., *Nat Biotechnol*, 18:62–65, 2000.
Haffter et al, The identification of genes with unique and essential functions in the development of the zebrafish, Danio rerio, The Company of Biologists Limited, 1999, pp. 1–17.
Driever et al, A genetic screen for mutations affecting embryogenesis in zebrafish, The Company of Biologists Limited, 1996, pp. 37–46.

* cited by examiner

*Primary Examiner*—Q. Janice Li
(74) *Attorney, Agent, or Firm*—Nixon Peabody LLP

(57) ABSTRACT

The present invention provides fish system as a powerful forward genetic tool to directly identify a number of novel genes involved in cell proliferation in vertebrates without the time consuming and costly maintenance of animals. The invention provides a tool to identify functional characteristics of a protein without prior knowledge of the gene sequence. After identification of the mutant gene in the fish system, the nucleic acid sequence of the gene can be used for identifying a homologue of the gene in another species, for example, in humans.

12 Claims, 29 Drawing Sheets

12 HPF

16 HPF

24 HPF

48 HPF

H3 ANTIBODY 24 HPF

ACRIDINE ORANGE 24 HPF

CONTROL

15 MIN POST-RADIATION

30 MIN POST-RADIATION

60 MIN POST-RADIATION

120 MIN POST-RADIATION

300 MIN POST-RADIATION

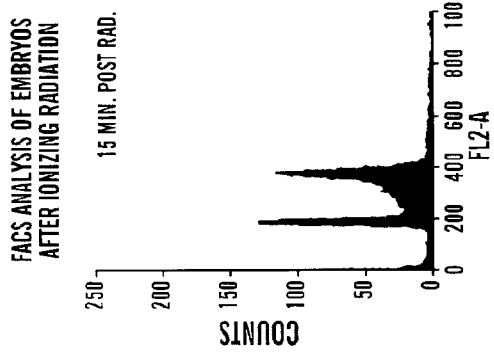
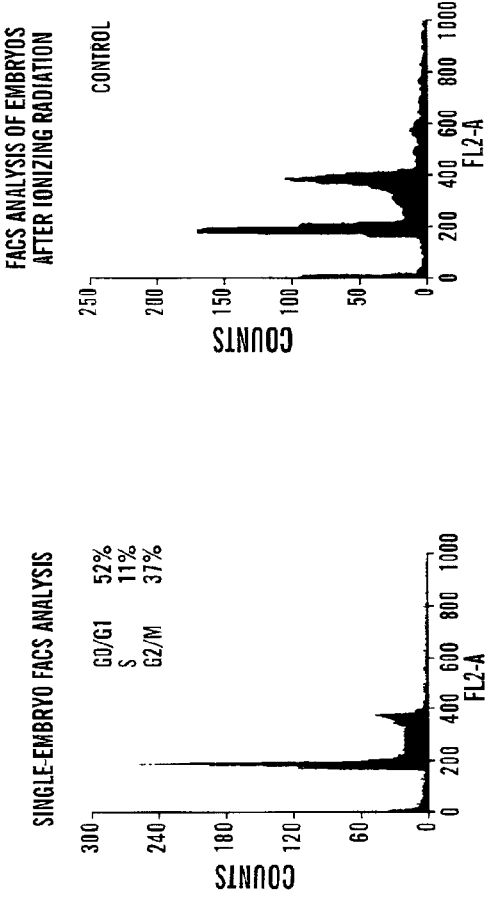
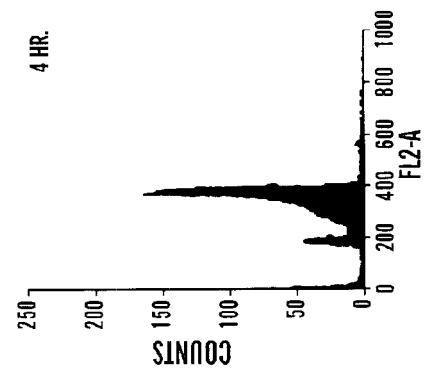
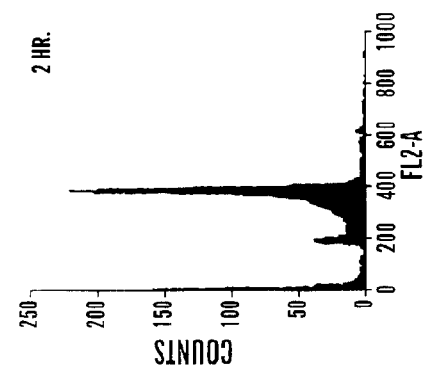
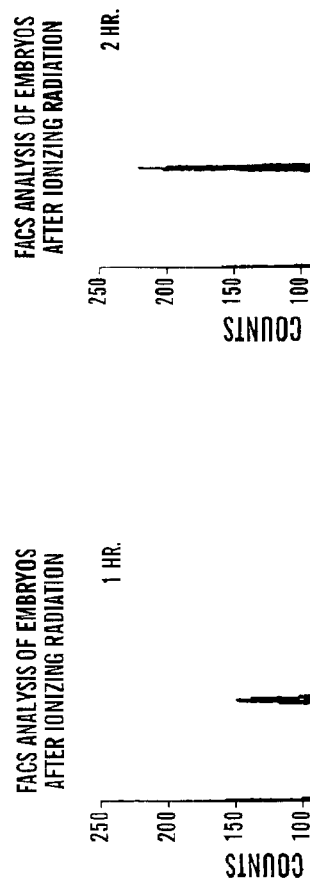
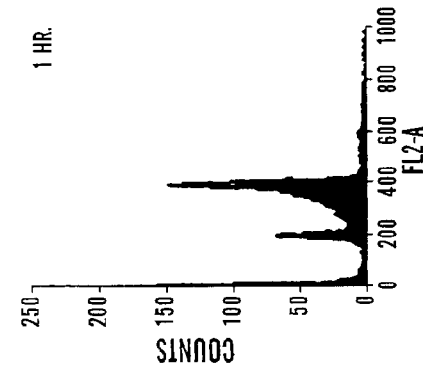

```
Zfish  MPPK--KRSSGTPQKKELKGSLKSRSPDSGDN----------AVLSPERHKDKDPEGVFLSEELQSTNSICDHAYRIMKR  68
Frog   MPPKSPRK---QQIRSQGEPRSPDRP-----------------------DFQQPDENFLCENLKISDNVRGKAWNTYGK  53
Human  MPPKTPRKTAATAAAAAAEPPAPPPPPPPEEDPEQDSGPEDLPLVRLEFEETEEPDGTALCQKLKIPDHVRERAVLTWGK  80

Zfish  EIRSMDK-TNMPYSNRQQWGALLFIAGMELEGINLIFIQFLKAVGLSVKQFISLVRKMDVNVDTISPKVNSAVTRLENSY  147
Frog   MFPSGYMMRE-TAKKKESLGLGLYLASVDCEEMTFTFTELLKILRLSVNRCFRLREMDINMDVLSNKVDHAISKLKKKY  132
Human  VSSVDGVLGGYIQKKKELWCICIFLAVDLDEMSFTFTELQKNIEISVHKFFNLLKEIDT-----STKVDHAMSPLLKKY  155

Zfish  DVTLALYQRFVKICEKIFAEPDNA-------KRKELWESSATMFLLAKGTFLQVEDDLVISFQLLLCVLEFFARRLSFSL  220
Frog   ENMCLLFQKFQRTFFSLIFEEQHNT---RAAVDTAPILKGTWITFLLARGKILQADDELVISSQLLLCVLDYFIKLSPSSI  209
Human  DVLFAIFSKLERICSLIYLTQPSS-SISTEINSALVLKVSWITFLLAKGEVLQSEDDLVISFQLMLCVLDYFIKLSPPML  234

Zfish  LQSPYNSVVSSSTLSPPTRTSPFNGGKSKPR--PAEMDMQLLETLCKEGDCSVDEVKNVYQSTFCAFLDSVCLLGLQCLP  298
Frog   LKEPYKSALNGLPVNTPPPSSRFSQNRNTRVSPQSFTDSKVLEFLCSQNYCPMDEVRNVYSTSFVDFLASACISSNEKIP  289
Human  LKEPYKTAV--IPINGSPRTPRFGQNRSARIAKQLENDTRIIEVLCKEHECNIDEVKSVYFKNGIPFMNSLCLVTSNGLP  312

Zfish  PMEALSKQYEELHHYSQIFDARLFLSDEILSPNKIEVSKVEVIPRKNLFAEDIAIPVEQTBIEAAATSIXQLRGDITEG  378
Frog   KVESISRQYEELIHHRMDLDARLFLENSETLKVDVQDSLDLERIPRKD--ESEVFPVPEQIAVGAANTVQQLMVTLSSA  367
Human  EVENLSKRYEEIQLHNILDARLFLDHKITQTDSIDSFETQRIPRKSNLDEEVNVIPGHIEVBTWNTIQQLMMILNSA   392

Zfish  SDQPSSNLLVYYKNCIVDPSGEIKKAVEELCEVHIQRFAQAVGHGEGLGRKSFYLCAQLYYKVMESMLKSEEKRLSVQA  458
Frog   NDKPPDTLDSKFSNCIVNKKTKGTDSIEHFPHVKEKFASSVECACAEICYQSYKLCVCLYYRVMEAILKNTEEERLSVHN  447
Human  SDQPSENLISLFNNCIYNGKESILKRVKDIRYIEKEKFAKAVEGCGVEICSQSYKLCVRLYYRVMESMLKSEEERLSIQQ  472

Zfish  FSKLLRNAAFFTSLLACALEVVIATYVGSSLKNGGFGRSSGASDSVESDLCFPWILSVFQLPAFDFYKVIECFIKAEPTL  538
Frog   FSKLLNNDIFFIQLLACAMEVVMASMARNA--------SQAYC-SSGTNLSFPWILRAFEIKAFDFYKVIECFIKAEPSL  518
Human  FSKLLNDNIFKMSLLACALEVVMGTYSRST--------SQN--LDSGTDLSFPWILNVLNLKAFDFYKVIESFIKAEGN  542

Zfish  KHDVVKHLEQCEHVIMFSLAWRADSPLFDLLKQSRE-EGPGEQAFPPATLNQELHHNHTAADLYLSPVPPCRQ-------  610
Frog   TSNMIKYLERCEHQIMECLAWQSDSPLFDLIKQTREREGLVDHPELVSNLQQFVQHNHTAADLYLSPSRSSHQHPVTSVP  598
Human  TREMIKHLERCEHRIMESLAWLSDSPLFDLIKQSKDREGPTDHLESACPLNLELQNNHTAADNYLSPVSPKKKGSTTRV  622

Zfish  --P-PVMEAEPPTP--GTRAPRSNSLSLFYKKLRMAYLRLKMIFSNLITSHPEMEPIIWTLLQHTLQNEYELMRDRHLD  685
Frog   TSSVTNGQVSSSQPVQ----QKSTSLSLFYKKMYLLAYKRLSSLCSSLLSDHPELEQVIWTLLQHTLQQEYELMRDRHLD  674
Human  NST-ANAETQATSAFQTQKPLKSTSLSLFYKKVIRLAYLRLNTLCERLLUSEHPELEHIIWTLFQHTLQAEYELMRDRHLD  701

Zfish  QLISSAMYAICKVKMVDLRFKTIVTAYKELPNTNQETFKRVLIREGQYDSIIVFYNLVFMQKLKTNILQYSSPRPCPLSP  765
Frog   QIMVCSMYGICKAKKIDLRFKTLVTAYKGLTNTKQETFKHVLIRDGQHDSIIVFYNLVFMQKLKSHILQYGSARHFTLSP  754
Human  QIMVCSMYGICKMKKIDLFKTIVTAYKDLPHAVQETFKRVLIKEEEYDSIIVFYNSVFMQRLKTNILQYASTRPPTLSP  781

Zfish  IPHIPCSPYK--NSPLRVPCSNNVYMSPLKSSRV------SPLVMTPRSRILISIGESFGSADKFQKINQKVSSSDWSLK  837
Frog   IPHIPRSPYRFGNSP-KVPC--NIYVSPLKTPYKTADGLLSPSKMTPKTSFLISLGETFRSPDRFQKINQLLNSCERPIK  831
Human  IPHIPRSPYKFPSSRLRIPCGN-IYISPLKSPYKISEGLPTPTKMTPRSRILVSIGESFGTSEKFQKINQKVCNSDRVLK  860

Zfish  RSLDGGSAPKPLKKRLRFDMDGQDEADGSKS-SGESALIQKLAENSSTRSRMQEQKLKEESDKDHPFP. SEQ ID NO: 1  904
Frog   RSADTGTTPKPLKKKLRFDSDGQDEADGSKHIQGESKFQQKLAEMTSTRTRMQKQKLEESLESSQQEEK SEQ ID NO: 2  899
Human  RSAEGSNPPKPLKKKLRFDIEGSDEADGSKHLPGESKFQQKLAEMTSTRTRMQKQKMNDSMDTSNKEEK SEQ ID NO: 3  928
```

*FIG. 11*

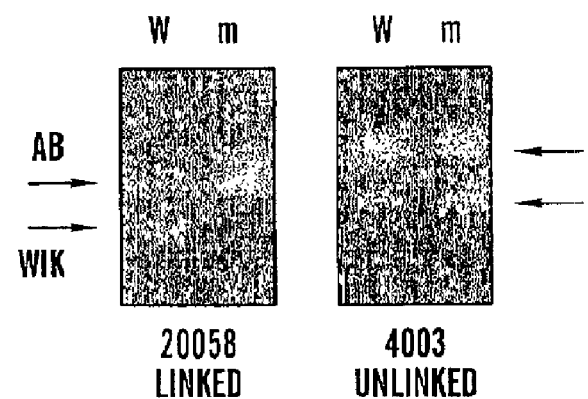
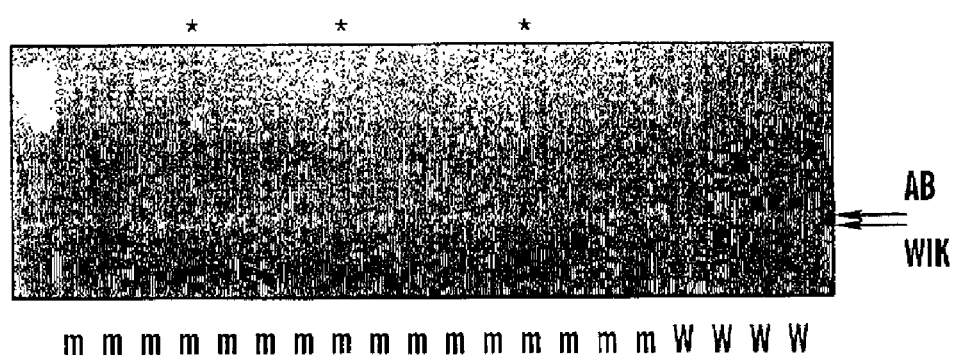
FIG. 14

METHOD FOR IDENTIFYING GENES INVOLVED IN CELL PROLIFERATION

FIELD OF INVENTION

The present invention discloses a method for identifying genes involved in cell proliferation using a fish model. The preferred fish model is a zebrafish.

BACKGROUND OF THE INVENTION

Cell cycle is a fundamental program that exists to precisely regulate mitotic fidelity and cell proliferation in uni- and multi-cellular organisms. The basic stages of the cell cycle are conserved from yeast to humans and include G1, S, G2, and M. Significant clinical, genetic and cell biologic evidence shows that disruption of cell cycle regulation results in aberrant cell proliferation and is central to carcinogenesis. For example, human tumor specimens frequently demonstrate an increased mitotic index, as shown by increased BrdU incorporation and PCNA expression. In addition, most oncogenes directly affect cell proliferation, acting as transmembrane receptors (ERBB, RET), membrane-bound (SRC, RAS) or cytoplasmic (ABL) signaling molecules, or transcription factors (MYC, JUN).

Many genes control the processes required for normal cell proliferation and when these genes are mutated, abnormal proliferation and tumor formation result. In humans, only a few genes in this complicated process have been characterized and a screening method of identifying genes specifically involved in cell cycle using a forward genetic approach would be advantageous.

Mice offer some advantages as a model organism for the study of cancer genes. Many homologues of the cloned human tumor suppressor genes have been mutated in the mouse [McClatchey, A., et al., *Curr Opin Genet Develop*, 8:304–310, 1998]. By obtaining strains carrying germline disruptions of these genes, both the heterozygous and homozygous phenotypes can be studied. Mice having heterozygous loss-of-function mutations represent models of humans with familial cancer syndromes and can serve as a model system for study of the progression of cancer. Additionally, the homozygous mutants can reveal developmental roles of these tumor suppressor genes. The generation of mouse strains with combinations of tumor suppressor gene mutations provides information about the genetic interactions in tumorigenesis. Transgenic mice expressing oncogenes provide information about the effects these genes have on proliferation and differentiation [Eva A., *Semin Cell Bio*, 3:137–45, 1992]. However, mice are not ideal animals for forward genetic studies to help to identify genes by their function as the number of mice needed for performing a genome-wide screen for recessive mutations is difficult and costly to maintain [Hrabe de Angelis M. et al., *Mutat Res*, 400:25–32, 1998].

*Drosophila* is another genetic model system for the study of cancer. The first mutant gene was identified as lethal (2) giant larvae gene (1(2)g1) and showed homology to a human gene [Mechler B. M, et al., *EMBO J*. 4:1551–57, 1985]. Genetic screens have identified mutations in over 50 genes in larval and adult stages [Watson K L, J. R., et al., *Cell Sci Suppl*, 18:19–33, 1994]. Many of these germ-line mutations cause embryonic lethality in homozygous animals, so screening for additional genes has been done in mosaic flies [Xu T., et al., Development, 121:1053–63, 1995]. Genes identified in this screen, such as LATS (large tumor suppressor), have proven to be relevant in mammals since knockout LATS-mice develop soft tissue sarcomas, ovarian tumors and pituitary dysfunction [St John, M. A., et al., *Nat Genet*, 21:182–186, 1999]. However, although *Drosophila* has revealed important genes involved in cancer, *Drosophila* tumor pathology does not closely resemble human tumors. Therefore, it would be an advantage to have a vertebrate forward genetic system to study cancer development that more closely resemble humans.

Fish have been utilized in laboratory carcinogenesis studies to evaluate the risk from environmental hazards [Couch, J., *Toxicol Pathol*, 24:602, 1996]. Zebrafish have been an integral part in these studies, and therefore much is known about carcinogen effects and tumor formation in this species. Zebrafish are known to develop numerous types of tumors, both naturally and through induction from genotoxic agents [Spitsbergen J. M., et al., *Toxicol Pathol*. 28:716–25, 2000; Khudoley, V. V., *Natl. Cancer Inst. Monogr*, 65:65–70, 1984]. Recently, transgenic zebrafish have been used for detecting mutations induced by particular compounds [Amanuma, K., et al., *Nat Biotechnol*, 18:62–65, 2000].

SUMMARY OF THE INVENTION

The present invention provides fish system as a powerful forward genetic tool to directly identify a number of novel genes involved in cell proliferation in vertebrates without the time consuming and costly maintenance of animals. The invention provides a tool to identify functional characteristics of a protein without prior knowledge of the gene sequence. After identification of the mutant gene in the fish system, the nucleic acid sequence of the gene can be used for identifying a homologue of the gene in another species, for example, in humans.

The identified genes are useful as diagnostic tools for analysis of human cell cycle defects such as cancer. The genes can be used in preparing constructs for production of specific antibodies against the peptide encoded by the newly identified gene. The antibodies can further be used as diagnostic tools in identifying cell cycle defects. One may also create an array consisting of several genes involved in cell cycle regulation and use the array as a diagnostic tool to simultaneously analyze problems in a variety of cell cycle regulating genes to determine the specific cell cycle defect in, e.g. a human affected with cancer thereby allowing a more targeted treatment plan. The newly identified genes involved in cell cycle regulation are also useful in drug screening assays and molecular modeling to identify targeted inhibitors or activators for the genes.

In one embodiment, the invention discloses a method of identifying a gene involved in cell proliferation comprising the steps of (a) exposing a fish to a mutagen; (b) mating the fish with a wild-type fish to produce an F1 generation; (c) exposing the eggs of the F1 generation to inactive fish sperm to produce haploid embryos; and (d) screening the haploid embryos for cell cycle defects wherein embryos with cell cycle defects harbor mutant genes involved in cell proliferation. In a preferred embodiment, the fish is a zebrafish. In a further preferred embodiment, the fish of step (a) is a male fish. The mutagen may be radiation or any mutagenic agent. In a preferred embodiment, the mutagen is an alkylating agent. In a most preferred embodiment the alkylating agent is ENU or MNU.

In another embodiment, the F1 generation is further mated with a wild-type zebrafish to produce an F2 generation which is raised to adulthood. The F2 generation is further back-crossed by mating a female member of the F2 generation with a male member of the F2 generation to produce F3 generation embryos. The F3 diploid embryos are then screened for cell proliferation defects. The embryos that show abnormal cell proliferation indicate that that specific strain harbors a gene involved in cell proliferation.

In one embodiment, the screening of embryos for cell proliferation defects is performed using an antibody raised against proteins involved in cell cycle. In the preferred embodiment, the antibody is raised against a protein selected from the group of phospho-histone H3, phosphorylated MAP kinase, phosphorylated MEK-1, BM28, cyclin E, p53, Rb and PCNA. In the most preferred embodiment, the antibody is directed against phospho-histone H3.

In another embodiment, the screening of embryos for cell proliferation defects is performed using a nucleic acid probe that recognizes a component of the cell cycle. In the preferred embodiment, the nucleic acid probe recognizes PCNA or cyclin b-1.

In one embodiment the screening is performed using flow cytometry. In another embodiment the screening is preformed using apoptosis markers including but not limited to Annexin V, TUNEL Stain, 7-amino-actinomycin D and Caspase substrates.

In yet another embodiment, the screening is performed using BrdU incorporation. In another embodiment the screening is performed using tubulin staining.

In a further embodiment the gene identified as being involved in cell proliferation is isolated, for example, using positional cloning methods. The isolated gene may consequently be sequenced and used to identify a homologue of the gene in another species, for example, in humans. The thereby identified genes and polypeptides encoded by them are useful targets for treatment of diseases related to abnormal cell cycle regulation such as various types of cancer.

Another embodiment of the present invention provides a method of identifying a gene involved in tumorigenesis using a carcinogenesis assay comprising the steps of (a) exposing a fish to a mutagen; (b) mating the fish with a wild-type fish to produce an F1 generation; (c) mating the F1 generation with wild-type fish to produce an F2 geneation; (d) exposing a wild-type fish and a member of the F2 generation to a carcinogen; and (e) comparing the tumor formation in the wild-type and the member of the F2 generation fish wherein an accelerated tumorigenesis in the F2 generation fish indicates a mutation in a gene is involved in tumorigenesis. In yet a further embodiment, the gene involved in tumorigenesis is isolated using, for example, positional cloning techniques.

BRIEF DESCRIPTION OF FIGURES

FIGS. 7(A)–(L) show defects in cell cycle on a series of mutants using FACS. (A) A FACS analysis of a single zebrafish embryo. (B) FACS analysis of gamma irradiated zebrafish embryos. (C) DNA content analysis of mutants SQW 226, SQW 319, and SQW 61 demonstrating aberrant cell cycle including endoreduplication shown as extra peak in SQW 226; populations of larger cells in both SQW 226 and 61; an increase in the G2/M cell population in SQW 319; and an increase in GI population in SQW 61.

FIG. 11 shows an alignment of a zebrafish, Xenopus, and human retinoblastoma tumor suppressor gene (Rb).

FIG. 14 demonstrates a microsatellite marker analysis of zebrafish DNA on agarose gel. W=wild-type; m=mutant; AB=; WIK=wik-strain.

FIG. 16(A) shows an outline of a dominant tumor suppressor screen. FIG. 16(B) shows an outline of a recessive enhancer-suppressor screen.

FIG. 17(A) is a 400× magnification of a normal liver sample. FIG. 17(B) is a 100× magnification of a tumor and FIG. 17(C) is a 400× magnification of the tumor.

FIG. 18(A) is a 400× magnification of a normal testis sample. FIG. 18(B) shows a 100× magnification of a testicular tumor and FIG. 18(C) is a 400× magnification of the tumor.

FIG. 19(A) shows a wild-type embryo with a normal spindle formation. FIGS. 19(B) and (C) show SQW 280 mutant where multiple spindle formation is seen. FIGS. 19D) and (E) show SQW 226 mutant where the spindle formation is disorganized. Both mutants appear to have cells with multiple nuclei.

FIG. 20(A) shows BrdU incorporation in a wild-type embryo. FIG. 20(D) shows mutant SQW 226 demonstrating moderately decreased BrdU incorporation and FIG. 20(F) shows mutant SQW 319 with severely decreased BrdU incorporation. FIG. 20(B) shows BrdU incorporation in mutant SQW 61; FIG. 20(C) shows BrdU incorporation in mutant SQW 213 and FIG. 20(E) shows BrdU incorporation in mutant SQW 280.

FIG. 21(A) shows Acridine Orange staining of a wild-type embryo. FIG. 21(B) shows Acridine Orange staining of mutant SQW 213; FIG. 21(C) shows Acridine Orange staining of mutant SQW 280; FIG. 21(D) shows Acridine Orange staining of mutant SQW 61; FIG. 21(E) shows Acridine Orange staining of mutant SQW 226; FIG. 21(F) shows Acridine Orange staining of mutant SQW 319. All the mutants demonstrate increased apoptosis compared to the wild-type.

DETAILED DESCRIPTION OF THE INVENTION

Figure 1:
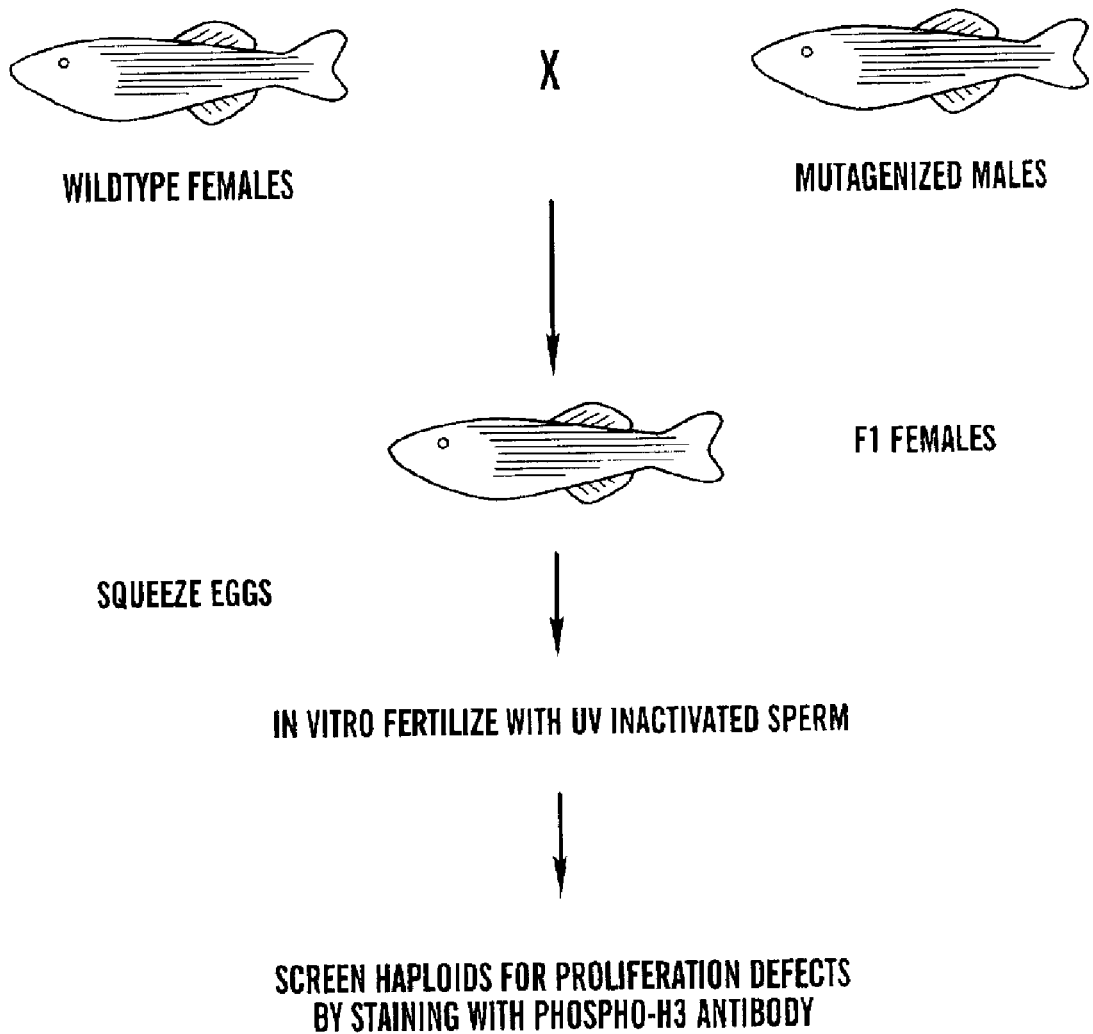
FIG. 1 is a schematic presentation of the zebrafish haploid screen for identifying genes with cell cycle mutations.

The present invention provides fish system as a powerful forward genetic tool to directly identify a number of novel genes involved in cell proliferation in a vertebrates without the time consuming and costly maintenance of animals. The fish useful according to the invention include but are not limited to zebrafish (*Danio rerio*), medakafish (*Oryzias latipes*) and fathered minnow (*Pimephales promelas*). In the preferred embodiment, the fish is zebrafish.

The zebrafish is a striped 2-inch long fish from the Ganges River. As a model system zebrafish provides significant advantages including external development and fertilization, optical clarity of the embryo, and ease of manipulation. In addition, its high fecundity (usually a few hundred but as many as 1000 eggs), short generation time, i.e., time from fertilization to gastrulation is only about 5 hours at 28° C.; somites form between 10–20 hours; and by 24 hours post-fertilization, a recognizable animal with rudimentary eyes and brain is formed. Also ease of mutagenesis and the ability to store large numbers of fish in a relatively small area strengthen its genetic potential. A number of mutations have already been identified from zebrafish and the mutant genes have been cloned. Several of the resulting genes have been homologues of human disease genes. For example, fish model systems now exist for such diseases as sideroblastic anemia [Brownlie, A., et al., *Nat genet*, 20:244–250, 1998].

Cell cycle in zebrafish is regulated similarly to other vertebrates exhibiting G1, S, G2, and M stages. In addition, the embryonic mitotic domains parallel those seen in, for example, *Drosophila* demonstrating the conservation of this mechanism. At the tenth cell cycle in zebrafish, the beginning of the mid-blastula transition occurs and the cell cycle lengthens [Kane, D. A., et al., *Nature*, 360:735–37, 1992]. Before that period, cell cycle length is roughly 15 minutes. After cell cycle 10, there is loss of cell synchrony and activation of zygotic transcription. Treating zebrafish embryos with nocodozolc results in destabilized microtubules and the activation of a mitotic checkpoint [Ikegami, R., et al., *Zygote*, 5:329–50, 1997; Ikegami, R., et al., *Zygote*, 5:153–75, 1997]. Camptothecin inhibits topoisomerase 1 and produces DNA strand breaks, resulting in subsequent apoptosis [Ikegami, R., et al., *Dev Biol*, 209:409–33, 1999]. Other agents such as hydoxyurea and aphidicolin also cause apoptosis. Thus, checkpoints similar to higher vertebrates are found in zebrafish. In addition, the zebrafish cell cycle machinery is highly similar to other vertebrates. Overall, zebrafish cyclin D1 is 77% identical to its human homologue and 88% identical in a region spanning 83 amino acids which is predicted to be the "cyclin box", a hallmark of G1 phase cyclins.

Zebrafish has been used as a genetic system and conditions for gamma-ray mutagenesis and screening are well-established [Chakrabarti, et al., *Brachydonio Genetics*, 103:109, 1983; Walker, et al., *Genetics*, 103:125, 1983]. ENU and EMS have also been used to induce mutations in isolated sperm from zebrafish [Halpern et al., *Cell*, 75:1, 1993; Solnica-Knezel, et al., *Genetics*, 136:1401, 1994].

In one embodiment, the present invention discloses a method of identifying a gene involved in cell proliferation comprising the steps of (a) exposing a fish to a mutagen; (b)

mating the fish with a wild-type fish to produce an F1 generation; (c) exposing the eggs of the F1 generation to inactivated fish sperm to produce haploid embryos; and (d) screening the haploid embryos for cell cycle defects wherein embryos with cell cycle defects harbor mutant genes involved in cell proliferation.

In a preferred embodiment, the fish is a zebrafish. In a further preferred embodiment the fish of step (a) is a male fish. FIG. 1 illustrates an outline of a haploid screen for cell cycle mutants. Mutagenized, for example ENU mutagenized males are mated with wild-type females. The F1 heterozygote females harboring point mutations are squeezed to produce haploid eggs that are fertilized with, for example, UV irradiated sperm, yielding development of haploid embryos. The embryos are screened for example at about 36 hours with, for example, an anti-phospho histone H3 antibody to screen for potential cell cycle mutant fish. The F1 females from clutches with significant amount change in staining, for example about 50%, are further studied.

Examples of mutagens that can be used in the step (a) include irradiation and chemical mutagenesis. Chemical mutagens are classifiable by chemical properties, e.g., alkylating agents, cross-linking agents, etc. The following four mutagens are particularly useful for mutagenesis of male germ cells: N-ethyl-N-nitrosourea (ENU); N-methyl-N-nitrosourea (MNU); procarbazine hydrochloride; chlorambucil. Other examples of useful chemical mutagens are as follows: cyclophosphamide; methyl methanesulfonate (MMS); ethyl methanesulfonate (EMS); diethyl sulfate; acrylamide monomer; triethylene melamine (TEM); melphalan; nitrogen mustard; vincristine; dimethylnitrosamine; N-methyl-N'-nitro-Nitrosoguanidine (MNNG); 7,12 dimethylbenzanthracene (DMBA); ethylene oxide; hexamethylphosphoramide; bisulfan. In a preferred embodiment, the mutagen is an alkylating agent. In the most preferred embodiment the alkylating agent is EMU or MNU.

For example, ENU mutagenesis of zebrafish can be performed essentially as described by Riley B. B. and Grunwald D. J. [*Proc Natl Acad Sci USA*., 92:5997–6001, 1995] or by van Eeden et al. [*Methods Cell Biol* 60: 21–41, 1999]. Shortly, male zebrafish are exposed to about 2.5–3.0 mM ENU in Embryo medium for one hour at 25° C. Fish are washed to two changes of fish aquarium water for one hour each wash. The treatment can be repeated about 3 and 6 days later. After exposure to mutagens, male fish are mated weekly to wild-type female fish. The F1 progeny generated 4–24 weeks after the last ENU treatment are used for screening.

After the mutagenesis the fish are mated with wild-type fish to produce an F1 generation of fish. Haploid embryos are produced by squeezing eggs from the female members of the F1 generation and exposing the eggs to inactive sperm. The term "inactive sperm", as used herein, indicates sperm that is incapable of fertilizing the egg but capable of inducing haploid embryogenesis. Inactive sperm can be produced, for example, by UV irradiation of zebrafish sperm. Also, sperm from a different fish species can be used. Haploid embryos allow phenotypic analysis of effects of point mutations on embryonal cell proliferation even in cases where the mutation would be recessive.

The haploid embryos are then screened for cell proliferation defects. Screening can be performed using a variety of methods. For example, embryos can be screened using immunohistochemical staining with an antibody recognizing a cell cycle component. The term "antibody", as used herein, means polyclonal, monoclonal or chimeric antibody, or an antigen recognizing fragment of an antibody. The antibody may also be labeled. Examples of labels include but are not limited to enzyme, biotin, chemical or fluorescent dye, and a radioactive residue. The term "cell cycle component", as used herein, means a protein participating in regulation of the cell cycle. Examples of known cell cycle components include, but are not limited to, the phosphorylated histone H3 (pH3), phosphorylated MAP kinase, phosphorylated MEK-1, BM28, cyclin E, p53, Rb, cyclin b-1 and PCNA.

For example, the screening can be performed using a phospho-histone H3 (pH3) antibody as illustrated in the FIGS. 2(A)–(D), 3(B) and 4(A)–(F). Embryos are first fixed. Several alternative methods for fixing are known for the skilled artisan. For example, 4% paraformaldehyde/PBS treatment overnight at about 4° C. Alternatively, fixing can be performed using Bouin's fixative [Bouin, *Arch. d'Anat. Micr.*, 1: 225, 1897] for one hour at room temperature; Dent fixative (20% Dimethyl sulfoxide (DMSO) in methanol) overnight at −20° C.; or the embryos can be stored in methanol at −20° C. After fixing, the unspecific antibody binding is blocked. Blocking can be performed using any number of techniques well known in the art. For example, embryos can be incubated for 30 minutes to one hour at room temperature with PBST and blocking reagents (10% heat treated lamb serum, 2% blocking reagent (Boehringer-Mannheim Biochemicals (Roche)) and 1% DMSO. Alternatively, blocking can be performed by incubating embryos for one hour in NCS-PBST (10% heat inactivated new-born calf serum in 0.1% Tween 20, 1% DMSO in PBS) in MABT. Optionally, the excess $2^{nd}$ antibody can be preabsorbed. For example, anti-mouse antibody can be diluted in 1:200 in a block solution, or an experimentally determined dilution, and incubated overnight at 4° C. with the embryos.

Figure 2A:
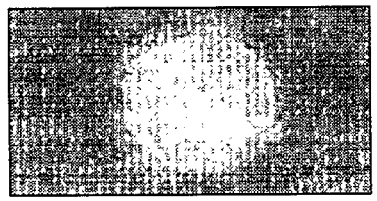
FIGS. 2(A)–(D) show an immunohistochemical staining of zebrafish embryos with a phospho-histone H3 antibody at various time points. The staining of zebrafish embryos is shown at (A) 12 hours; (B) 16 hours; (C) 24 hours; and (D) 48 hours of development.
Figure 2B:
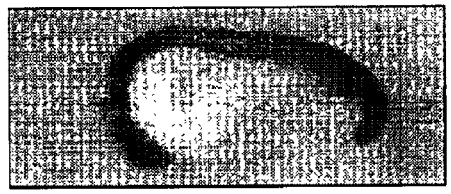
Figure 2C:
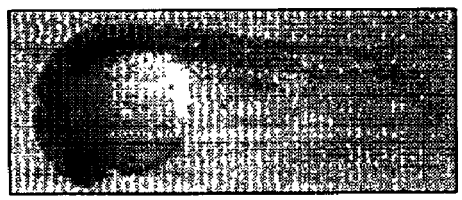
Figure 2D:
Figure 3A:
FIGS. 3(A)–(B) show mitotic and apoptotic cells in the eye of a zebrafish embryo. (A) A phospho-histone H3 immunohistochemical staining and (B) an Acridine Orange staining of 24 hours post fertilization zebrafish embryo eye showing (A) mitotic and (B) apoptotic cells.
Figure 3B:
Figure 4A:
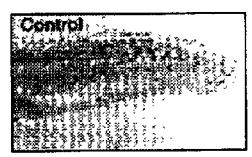
FIGS. 4(A)–(F) are a presentation of an experiment using phospho-histone H3 antibody in an immunohistochemical staining of a zebrafish embryo after gamma irradiation. The figure demonstrates that the mitotic arrest induced by irradiation peaks at 30–60 minutes and that the recovery to the normal number of mitotic cells is complete by 5 hours. The experiment shows (A) a control with no irradiation; (B) an embryo stained 15 minutes post irradiation; (C) an embryo stained 30 minutes post irradiation; (D) an embryo stained 60 minutes post irradiation; (E) an embryo stained 120 minutes post irradiation; and (F) an embryo stained 300 minutes post irradiation.
Figure 4B:
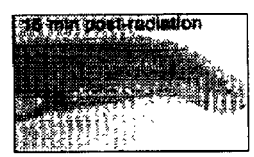
Figure 4C:
Figure 4D:
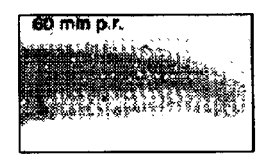
Figure 4E:
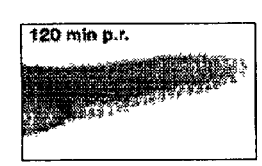
Figure 4F:
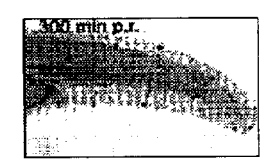

In FIG. 2(A)–(D), phospho-histone H3 antibody is shown to mark an increasing number of mitotic cells during the first 48 hours of zebrafish development. FIG. 3(A) illustrates that mitotic and apoptotic cells are contained within separate compartments of the zebrafish eye. FIG. 4(A)–(F) shows that gamma radiation induces a cell cycle arrest which leads to a decrease in the number of mitotic cells. This arrest peaks at 30–60 minutes post radiation and recovery to the normal number of mitotic cells in complete by 5 hours.

Another method of screening for cell cycle defects is flow cytometrical cell sorting or FACS whereby the DNA content of cells can be analyzed indicating the specific cell cycle phase [for details see e.g. *Flow Cytometry: A Practical Approach*. Edited by MG Ormerod. IRL Press, Oxford. 1994; *Practical Flow Cytometry*. 3rd Edition. Howard M Shapiro. Alan R Liss, Inc.].

The DNA of cells can be stained by a number of dyes. Examples include: Propidium iodide, ethidium bromide, Hoechst dyes, for example Hoechst 33342 and Hoechst 33258, Mithramycin, DAPI (4,6-Diamidino-2-phenylindole), 7-Aminoactinomycin D, TO-PRO-3, Chromomycin.

The most commonly used DNA dye is propidium iodide (PI), which intercalates in the DNA helix and fluoresces strongly orange-red. It has the advantage that it is excited by 488 nm light and can be used on most common flow cytometers. However it does require cells to be fixed or permeabilized and therefore non-viable. PI also stains double-stranded RNA and this should be removed with ribonuclease.

An alternative is to employ Hoechst 33342 which binds AT pairs in the DNA and will enter viable cells without the need for fixation, so cells can be recovered and grown afterwards. The rate of dye uptake is dependent on dye concentration and cell type.

Figure 7G:
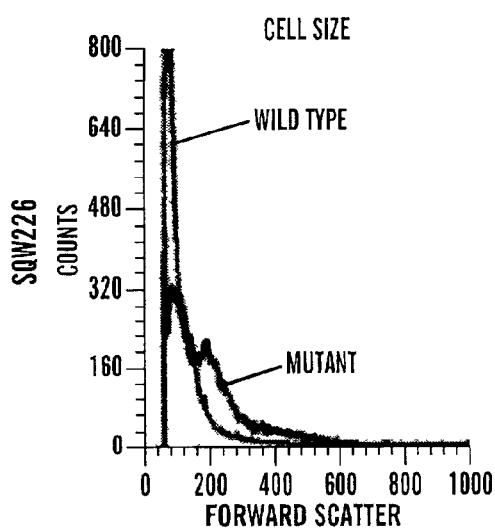
Figure 7J:
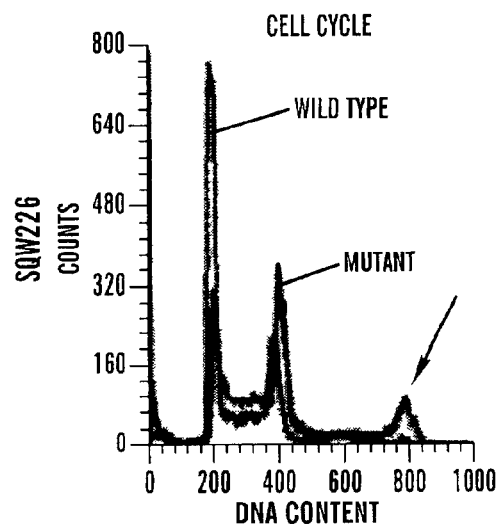
Figure 7H:
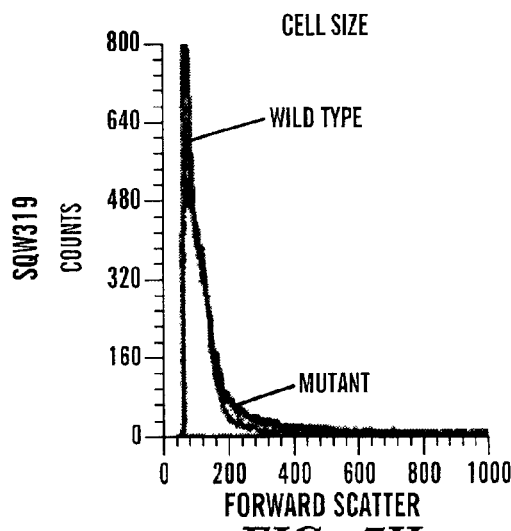
Figure 7K:
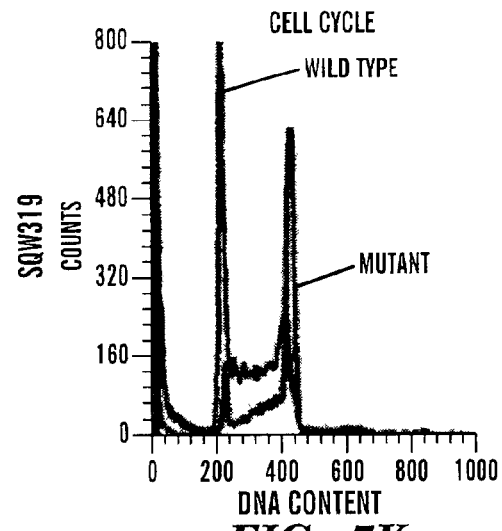
Figure 7I:
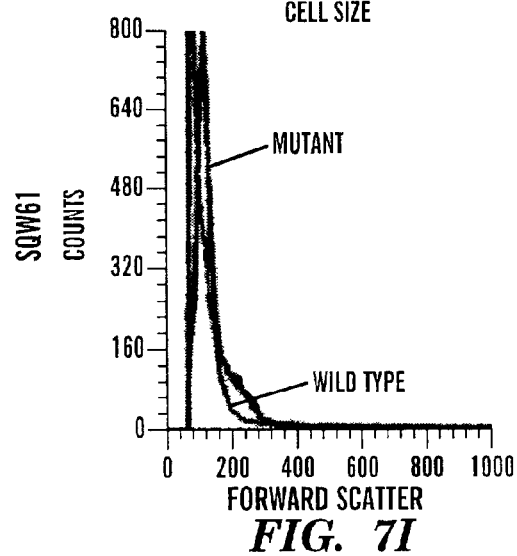
Figure 7L:
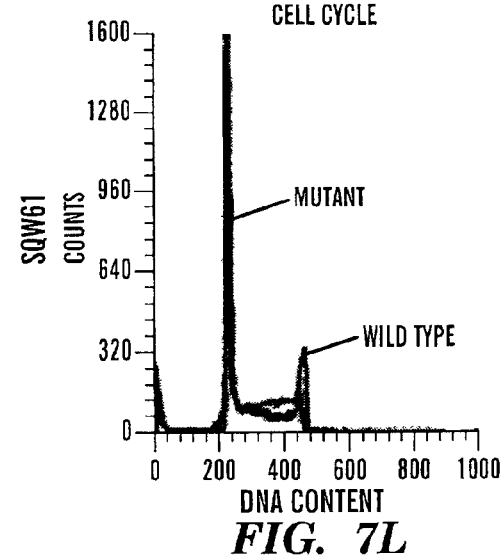

For example, wild-type and mutant embryonic cells were stained with propidium iodide and subjected to DNA flow cytometry (FIG. 7(A)–(C)). This analysis has been successfully performed on single embryos (FIG. 7(A)). Flow cytometric analysis of 24 hours post fertilization (hpf) zebrafish embryos after exposure to 1600 rads of ionizing radiation demonstrates accumulation of cells in G2-phase (FIG. 7(B)), indicating activation of the G2 DNA-damage checkpoint. Consistent with the known kinetics of eukaryotic DNA repair, reversal of G2 arrest is seen beginning at 2 hrs post-radiation. During this same time period, pH3 immunoreactivity is profoundly depressed, suggesting that the G2 radiation checkpoint precedes the onset of chromatin condensation and H3 phosphorylation. The analysis of SQW226 (FIG. 7(C)) and SQW 280 (not shown) demonstrates endoreduplication (arrow), a feature commonly found in human tumors such as neuroblastoma, suggesting that the increased pH3 staining in whole mount truly indicates an increase of cells at the G2/M boundary in vivo. SQW61 analysis showed a decrease in percent G2 and an increase in G1, suggesting a G1 arrest (FIG. 7(C)). DNA flow cytometrical analysis of SQW 319 showed an increase in G2, whereas pH3 staining was decreased.

Screening for cell cycle defects can also be performed using the "gold standard" carcinogenesis assay to determine which mutants are relevant to cancer biology. The carcinogenesis assay evaluates whether fish mutants are more prone to developing cancer than their wild-type siblings. The carcinogen should accelerate tumor development. Specific carcinogens can be used. Wild-type fry (3-week-old fish) have been exposed to the carcinogens 7,12 Dimethyl benzanthracene (DMBA) (doses 1.0, 2.0, 5 and 10 ppm) and N-methyl-N-nitro-N-nitrosoguanidine (MNNG) (doses 0.5, 1.0, 2.0 and 3.0 ppm) for a 24-hour period and then placed into fresh water and raised to adulthood. Survival is monitored and fish that die or look ill are fixed for sectioning. In other cases, an entire cohort is fixed for sectioning and pathological analysis at an arbitrary time point (usually 3, 6 or 12 months). This assay is based on a histologic analysis.

For example, in preliminary studies, carcinogen-treated zebrafish have developed medulloblastoma or germ cell tumors that closely resembles human disease (FIGS. 6(A)–(E)). In this manner, heterozygotes (or homozygous mutants, if viable) can be tested for propensity to cancer whereafter each mutant gene can be mapped. Tumorigenesis and death in the clutch can be studied by Kaplan-Meier statistical analysis (FIG. 6(E)).

FIGS. 17(A)–(C) and 18(A)–(C) illustrate histology of zebrafish tumors in liver (17) and testis (18). Fish were exposed to MNNG (5 ppm) and sacrificed after three months. Histological staining shows a tumor in liver (17(B)–(C)) and testis (18(B)–(C)). In testis, very large dysplastic cells, marked with an arrowhead in FIG. 18(B), were observed. The homozygous mutants that are prone to getting cancer can be subjected to dominant suppressor screens (see below). Alternatively, mutants that are heterozygous and prone to cancer can be subjected to enhancer-suppressor screens for recessive mutants as described below.

Figure 8A:
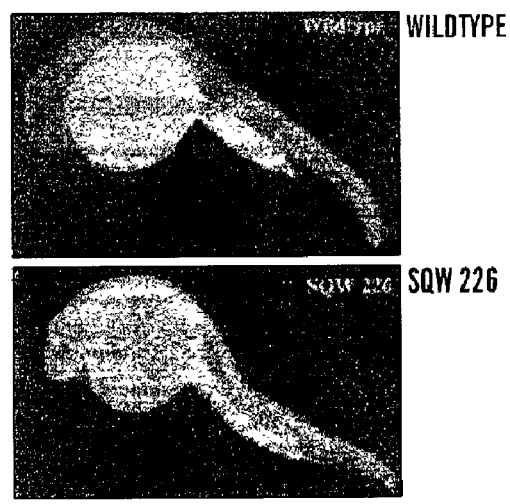
FIGS. 8(A)–(C) present the results from an analysis of the zebrafish mutant SQW226. (A) Increased number of cells undergoing apoptosis can be seen in the mutant (bottom) compared to the wild-type zebrafish (top). (B) BrdU-labeling of a wild-type (right) and mutant zebrafish (left). (C) BrdU incorporation after 10 minute chase period in a wild-type (top) and two different mutant zebrafish strains demonstrating that S-phase cells are decreased in mutants SQW 226 and SQW 319.

The screening may further be performed using markers detecting apoptosis as aberrant apoptosis is a sign of cell cycle defect [for examples see e.g. *Annu Rev Biochem* 69:217–45, 2000] We have developed several techniques for detecting apoptotic cells in the zebrafish embryo as illustrated in the FIG. 8(A). Acridine orange staining of SQW 226 demonstrates that the mutant has a significant increase in cell death at 24 or 36 hrs. It is likely that the cells with defective cell cycle undergo an apoptotic death. Each mutant was stained with acridine orange.

Lysotracker (Molecular Probes, Eugine, OR) is an aldehyde fixable red dye that also stains apoptotic cells in live embryos, and allows us to further study the mutants in conjunction with other probes. The mutants can also be studied for cell death by TUNEL staining. We have previously used these assays to demonstrate apoptosis of hematopoietic cells in the blood mutants. FIG. 8(A) shows a mutant SQW226 demonstrating an increased number of cell undergoing cell death as compared with wild-type. Heterozygous incrosses of SQW226 were performed. At 24 hours, it is apparent that one quarter of the clutch displays a "tail up" phenotype. These homozygous embryos were stained with the vital dye Acridine Orange and examined under an epifluorescent microscope to evaluate the extent of apoptosis. FIGS. 21 (A)–(F) demonstrate a significantly increased apoptosis in various zebrafish embryo mutants using Acridine Orange staining.

Figure 8B:
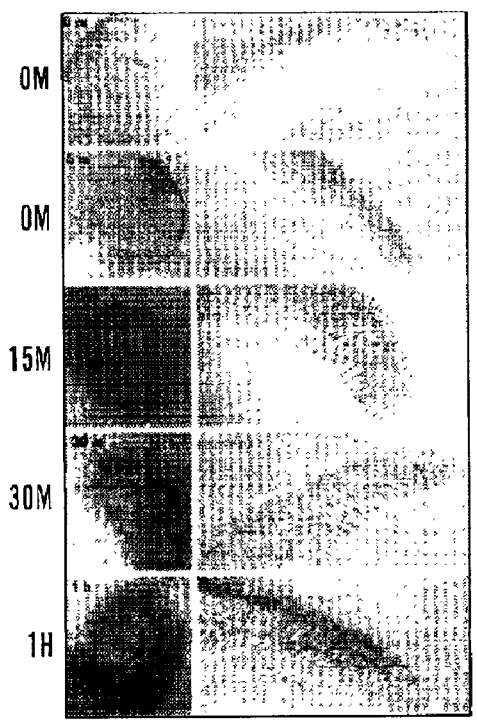
Figure 8C:
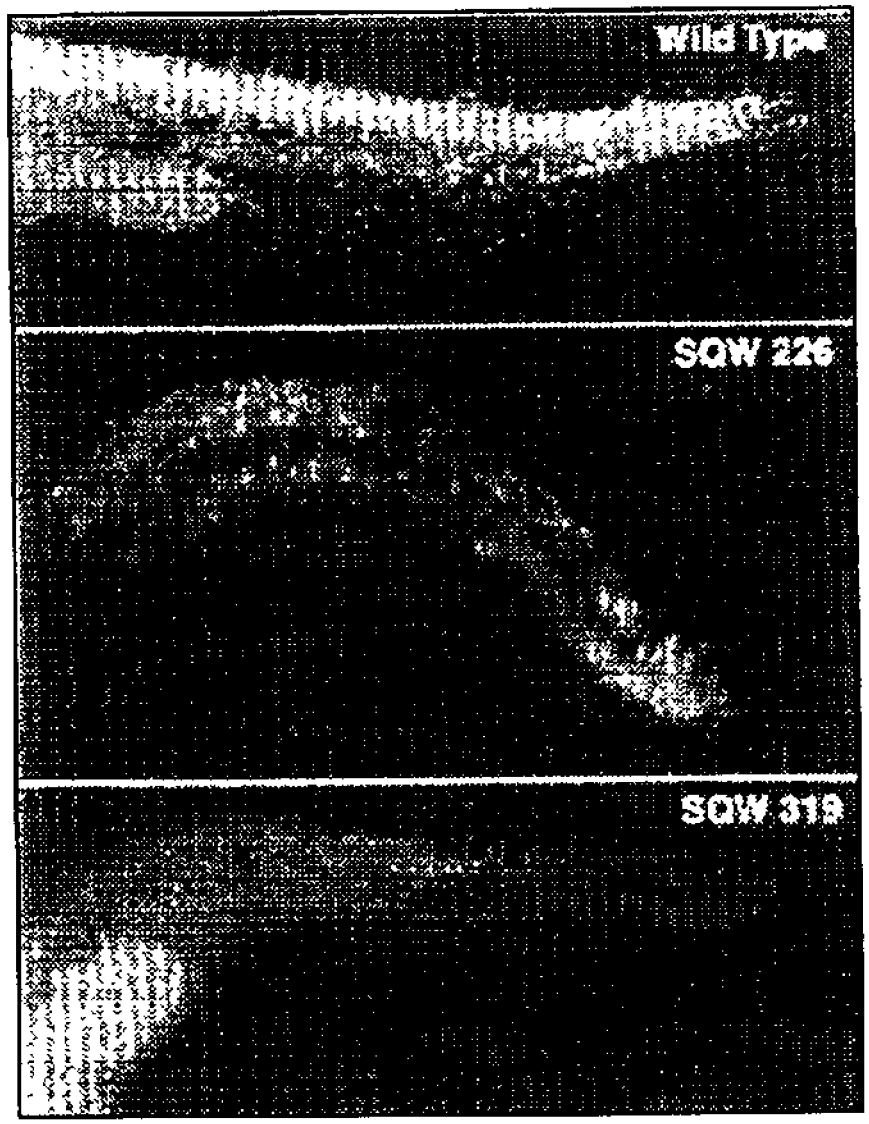

Cell cycle defects in fish embryos may also be detected using BrdU staining as a screening method. BrdU is incorporated into DNA by cells in S phase (FIG. 8(B)). This assay will allow refinement of the cell cycle phenotype. This information will be correlated to the DNA flow cytometrical analysis data and to the whole mount mutant phenotype of pH3 staining. These assays together should help define the stage in a cell cycle at which the mutant gene acts and more precisely determine the position of the cell cycle block. FIG. 8(C) shows the analysis of SQW 226 and 319, each demonstrating decreased incorporation of BrdU. FIG. 8 (B) shows BrdU labeling of wt and mutant zebrafish. Time course of BrdU labeling in wild-type zebrafish embryos. Live 24 hpf embryos were incubated in 10 mM BrdU on ice, rinsed and chased for the times indicated at 28.5° C. Details of labeling in the eye and tail are shown, demonstrating a progressive increase in labeled cells with longer incubations. FIG. 8(C) illustrates BrdU incorporation in wild-type and mutant embryos after a 10-minute chase period, demonstrating that S-phase cells are moderately and severely decreased in mutants SQW226 and SQW 319, respectively. FIGS. 20(A)–(F) demonstrates BrdU staining of zebrafish embryos 36 hours post fertilization and the defective staining is clearly seen in mutants SQW 226 (20(D)) and SQW 319 (20(F)).

Tubulin staining can also be useful in detecting defects in fish cell cycle. The mitotic spindle plays a vital role in the cell cycle, and the mutants could represent defects in this process. As such, it is important to define whether a cytokinesis defect is evident. Tubulin staining of the zebrafish has been used for examining mitosis. This technique has previously been used to characterize the retsina mutant in zebrafish that displays a cytokinesis defect in hematopoiesis which leads to bi-lobed nuclei in the peripheral blood. Analogous staining is done to evaluate whether spindle pole assembly and orientation are correct in each mutant. Tubulin staining may illustrate defects such as endoredublication which may also be detected using FACS (see below). FIGS. 19(A)–(F) demonstrate defective spindle formation in two mutants, SQW 280 in 19(B)–(C) and SQW 226 in 19 (D)–(E). In FIG. 19, monoclonal antibody against α-tubulin was used. Tubulin staining may be performed as described in Mitchison T. et al. in iProtocol at http://iprotocol.mit.edu/protocol/135.htm.

Figure 9:
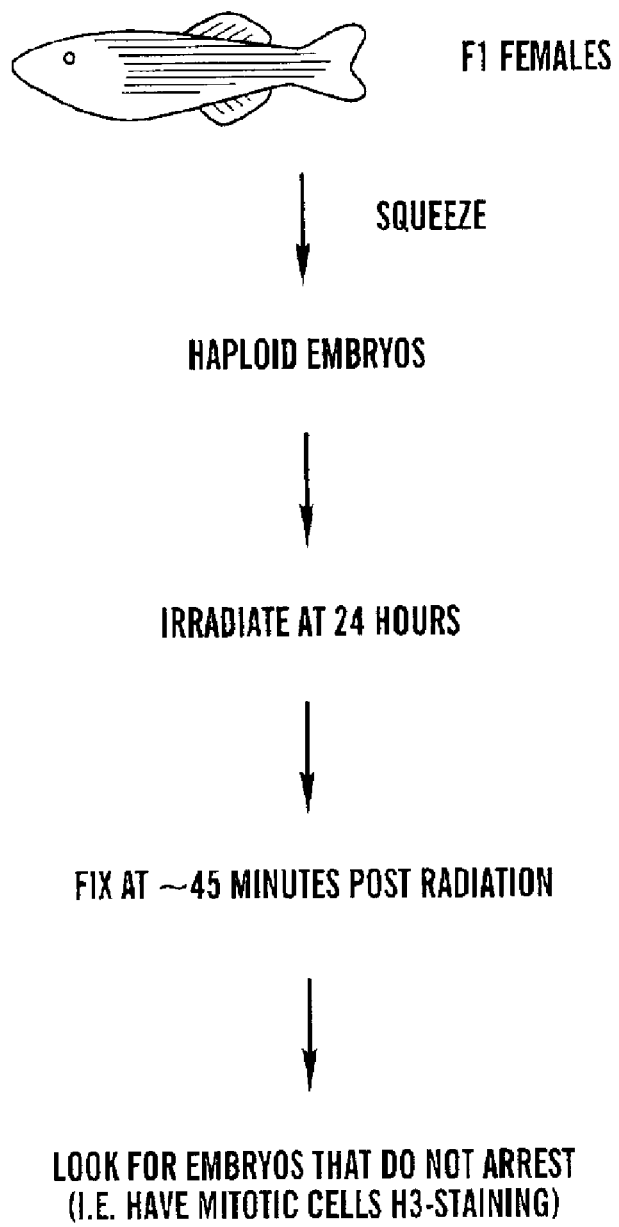
FIG. 9 is a schematic presentation of a haploid zebrafish embryo screen using gamma irradiation and consequent detection of mitotic cells to indicate embryos with cell cycle defects.

Fish can also be subjected to an irradiation analysis as a method of screening for cell cycle defects. For example, γ-irradiation of zebrafish embryos at 24–36 hpf with 800–1200 rads causes a cell cycle arrest as shown in FIG. 2(C), yet the embryo recovers and continues to develop normally (at least to 24 hours of age). pH3 staining decreases substantially to being barely detectable by 30 minutes post radiation (p.r.), but the staining recovers to normal levels at 2 hours post irradiation. DNA flow cytometrical analysis demonstrates an increasing proportion of cells in G2/M from 15 minutes p.r. to 4 hours p.r., suggesting a G2 arrest. To evaluate whether any of our mutants have checkpoint defects, we irradiated SQW226 (FIG. 10) and demonstrated that the homozygous mutants fail to display decreased pH3 staining. Therefore, either SQW226 is able to override a checkpoint or alternatively exhibits an exit block. In contrast, wild-types (+/− or +/+) had decreased pH3 staining after irradiation. Each mutant could be evaluated in this irradiation screen for cell cycle checkpoint defects. In addition, this irradiation screen forms the basis for doing a checkpoint or exit block screen on zebrafish embryos (FIG. 9).

Figure 10:
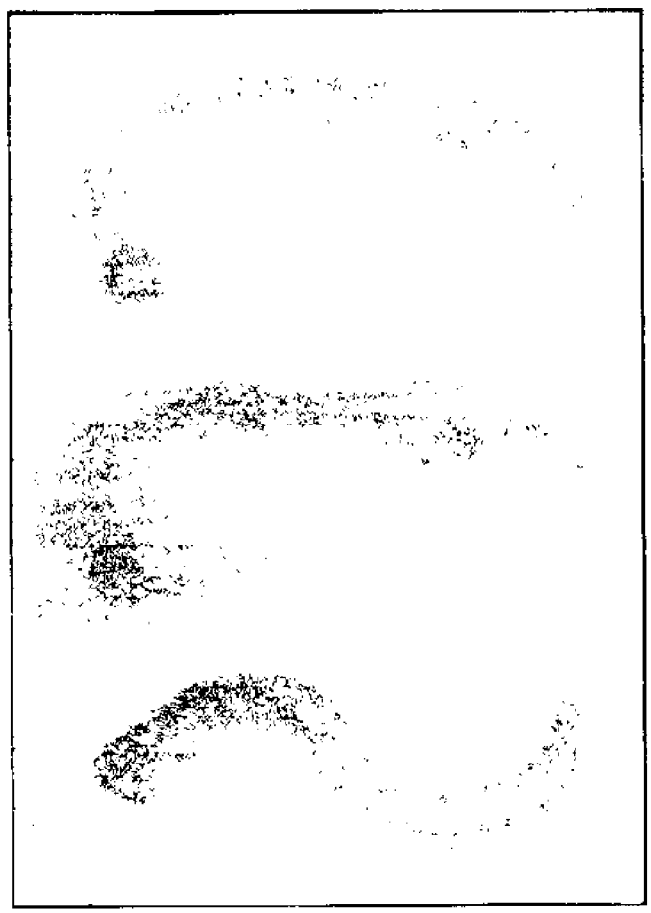
FIG. 10 shows zebrafish embryos after haploid screen using gamma irradiation and consequent detection of mitotic cells. Top: wild-type embryo without irradiation. Middle: wild-type embryo after irradiation showing decreased phospho-histone H3 staining indicating normal cell cycle arrest. Bottom: SQW 226 mutant embryo showing no decrease in phospho-histone H3 staining indicating either that the mutant is resistant to the radiation-induced cell cycle arrest or that the cell cycle is abnormally controlled.

FIG. 10 demonstrates that a mutant zebrafish embryo SQW 226 does not show a decrease in the number of mitotic cells (pH3 staining) in response to irradiation. This suggests that either SQW 226 is resistant to the radiation-induced cell cycle arrest or the cell cycle is blocked and shows no effect from radiation. FIG. 10 illustrates a haploid screen that can be performed based on the observed radiation-induced cell cycle arrest. Haploid embryos from F1 females (progeny of mutagen treated males and wild-type females) can be irradiated and fixed 45 minutes post radiation. These embryos can be stained with, for example, the pH3 antibody and mutants that do not exhibit the normal decrease in mitotic cells can be identified. These mutants are believed to represent cell cycle machinery or checkpoint control gene mutants and are therefore excellent models for the study of cancer formation and as subjects for modifier screens such as dominant suppressor or suppressor-enhancer screens described below.

Once the F1 generation fish females showing aberrant staining and therefore suggesting the potential mutations are identified, they are further out-crossed to wild-type males. The resulting F2 progeny is raised to adulthood and incrossed to re-identify heterozygote pairs and to confirm that the phenotype identified with any one or more of the above described screening methods can be recapitulated in the diploid state. Since the F2 families are 50% heterozygotes and the mating is done at random, at least about 20 clutches should be examined to attempt to recover the mutant phenotype in the F3 generation. If the phenotype does not appear in the first 20 clutches screened, then that particular family is unlikely to harbor a mutation. The F3 diploid embryos are fixed and stained as described above to score for abnormal cell proliferation phenotype.

Once a fish with a cell cycle defect has been identified, the genetic material, DNA, of the fish can be subjected to a linkage analysis and consequent positional cloning of the mutant or defective gene.

Nucleic acids, DNA or RNA, from the fish are isolated using methods well known in the art [see for example Sambrook, et al. Molecular Cloning: *A Laboratory Manual*, CSH Press 1989; Liao E. C. and Zon L., *Methods Cell Biol* 60:182–184, 1999].

The nucleic acid may be used without amplification or may be amplified by conventional techniques, such as the polymerase chain reaction (PCR), to provide sufficient amounts for analysis. A review of techniques used in performing the polymerase chain reaction may be found in Sambrook, et al. Molecular Cloning: A Laboratory Manual, CSH Press 1989. Amplification may also be used to determine whether a polymorphism is present, by using a primer that is specific for the polymorphism. Alternatively, various methods are known in the art that utilize oligonucleotide ligation as a means of detecting polymorphisms [for examples, see Riley et al. *Nucleic Acids Res* 18:2887–2890, 1990; Delahunty et al. *Am. J. Hum. Genet.* 58:1239–1246, 1996].

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P or $^{33}$P, $^{35}$S and $^{3}$H. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Mutants can be mapped onto zebrafish linkage groups by either determining centromeric linkage by half-tetrad analysis [Johnson, S. L., et al. *Genetics*, 139:1727–1735, 1995] or by scanning microsatellites for linkage. The half tetrad method involves following the segregation of known SSLP centromeric markers with respect to wild-type and mutant gynogenetic diploid embryos [Streisinger, G., et al., *Nature*, 291:293–296, 1981; Streisinger G., et al., *Genetics*, 112:311–319, 1986].

The mutation can also be assigned to a linkage group, by bulk segregation analysis with CA repeat markers [Talbot W. et al., in *Methods in Cell Biology* eds. H.I. Detrich, M. Westerfield, L. Zon, Academic Press, San Diego: 260–284, 1999; Liao, E. et al. Id. at 181–183]. For example, a wik background fish carrying the mutation (heterozygote) is mated to a polymorphic strain (AB). Haploid embryos are generated from heterozygous wik/AB hybrid females by fertilizing eggs with inactivated sperm. Alternatively, diploid embryos can be generated by mating heterozygous hybrid males and females. Either haploid or diploid embryos are scored as either wild-type or mutant by fixing and staining them with, for example, the anti-pH3 antibody. DNA is then isolated from individual embryos. Bulk segregation analysis is performed on wild-type and mutant pools of about 20 DNA samples (two wild-type pools and two mutant pools) (FIG. 11(A)). PCR is performed on these pools using, for example, CA-repeat primers from the linkage group indicated.

Fragments that amplify from both AB and wik DNA are uninformative; however, fragments that are polymorphic between the two strains can be used as positional markers. A linked marker will be identified as one that segregates in the pools, meaning that bands of different sizes are amplified from the wild-type as compared to the mutant pool. If a linked marker is found, it will be tested on individual embryos to determine the recombination frequency between the marker and the mutation.

Currently there are about 3000 CA markers available for the analysis of zebrafish. Therefore, it may be necessary to identify new markers because a closely flanking marker may not be found. AFLP analysis has proved to be a useful way to test many markers simultaneously. Testing 256 primer combinations can yield information on 6400 loci [Ghebranious N., et al., *Oncogene*, 17:3385–3400, 1990].

Microsatellite linkage analysis may be performed alone, or in combination with direct detection of polymorphisms. The use of microsatellite markers for genotyping is well documented [for examples, see Mansfield et al. *Genomics* 24:225–233, 1994; Ziegle et al. *Genomics* 14:1026–1031, 1992.]

Unique nucleotide sequences are selected from the DNA region flanking the repeat region and they are used as primers in PCR to amplify the region of genomic DNA that contains the repeats. Conveniently, a detectable label will be included in the amplification reaction either attached to a primer used in the amplification reaction or as a labeled nucleotide. Multiplex amplification may be performed in which several sets of primers are combined in the same reaction mix. This is particularly advantageous when limited amounts of sample DNA are available for analysis. Conveniently, each primer set may labeled with a different fluorochrome or alternatively, primers amplifying alleles of different size range may be selected for one amplification reaction mix.

After amplification, the products are size fractionated. Fractionation may be performed by gel electrophoresis, particularly denaturing acrylamide or agarose gels. A convenient system uses denaturing polyacrylamide gels in combination with an automated DNA sequencer [see e.g. Hunkapillar et al. *Science* 254:59–74, 1991]. Capillary electrophoresis may also be used for fractionation. A review of capillary electrophoresis may be found in Landers, et al. (1993) *BioTechniques* 14:98–111.

Figure 15:
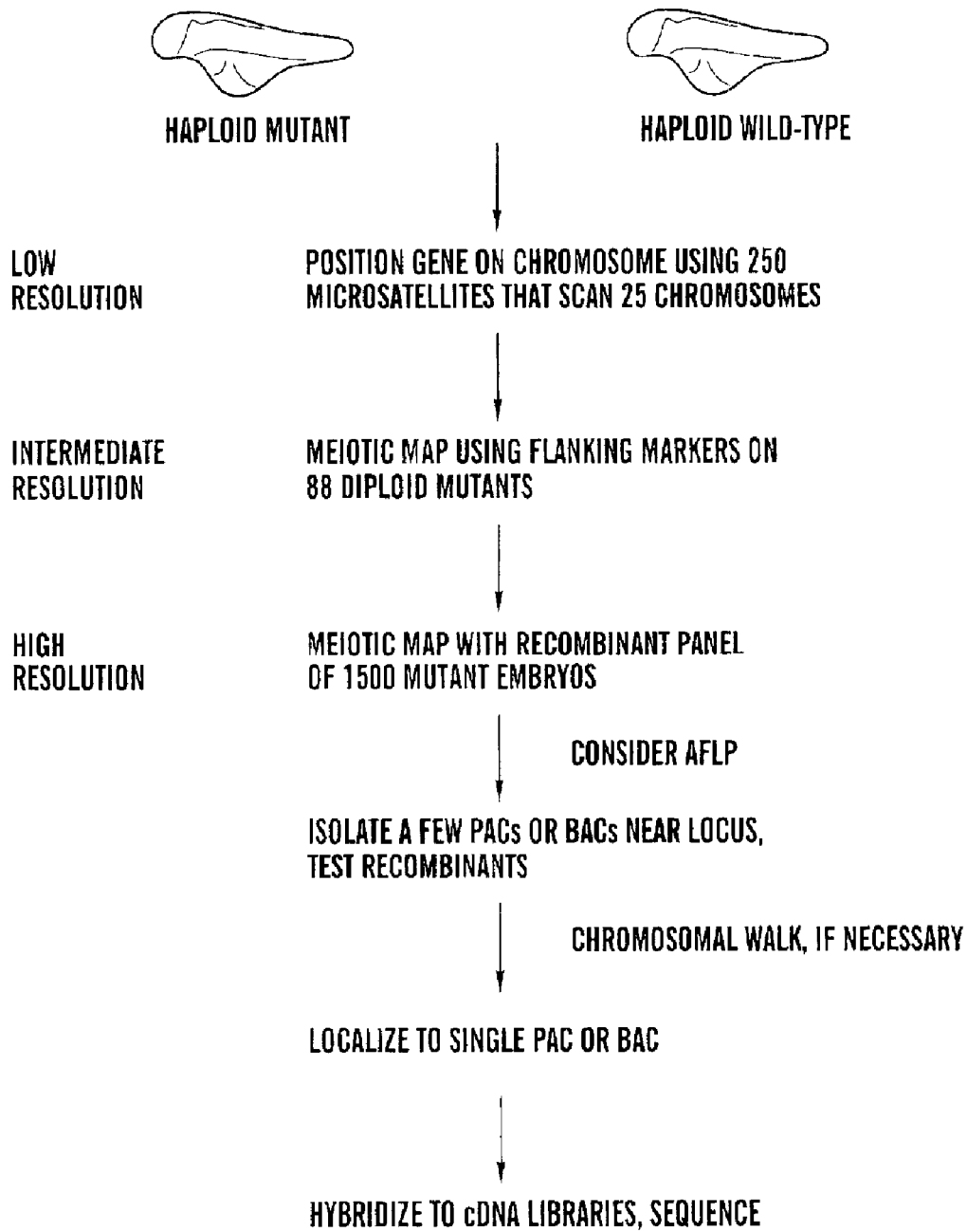
FIG. 15 is a schematic presentation of positional cloning of novel genes in fish involved in cell cycle regulation identified using linkage analysis.

FIGS. 14 and 15 demonstrate the linkage analysis approach using zebrafish. FIG. 15 shows an outline of a strategy to use microsatellite markers to generate low and intermediate resolution map positions for the mutants obtained from the screen. Markers found to be linked to the mutation are further analyzed on a panel of 1500 mutants to determine distance from the marker to the mutation (high resolution mapping) in order to initiate a chromosomal walk. PACs and BACs are isolated and the mutation are localized to a single genomic fragment. cDNA clones are then be isolated and analyzed to determine which contains the pertinent mutation. FIG. 14 shows an agarose gel with zebrafish microsatellite markers that are useful for linkage analysis. In pools (top), 20058 is linked to the mutation in question and 4003 is unlinked. On the bottom, individual embryos are used to show linkage.

Once a rough map position has been identified, there a generally two approaches to clone a gene: candidate gene analysis and positional cloning. [See Collins F., *Nat genet*, 9:347–50, 1995]. A candidate cloning approach can be used once the gene is localized to an as narrow region of a specific fish chromosome as possible.

Candidate approach relies on a three-step process that saves time and effort: (1) localizing a disease gene to a chromosomal subregion, generally by using traditional linkage analysis; (2) searching databases for an attractive candidate gene within that subregion; and (3) testing the candidate gene for disease-causing mutations. Candidate gene analysis is feasible when several known genes are located to the chromosomal locus identified using linkage analysis as described above. The genes are sequenced from a control fish and the mutant fish. If a mutation is identified in the mutant fish, it may be further analyzed in a variety of expression systems so as to determine if the identified mutation is causing the mutant phenotype.

The overall strategy of positional cloning is to map the location gene by linkage analysis and to then use the mapped location on the chromosome to clone (or copy) the gene. Positional cloning is used when no known genes are located in the chromosomal locus of interest. If expressed tagged sequences (ESTs) have been localized to the chromosomal region identified using linkage analysis they can be used as probes to clone a full genomic or cDNA clone from libraries containing either genomic fish DNA or cDNA prepared from fish MRNA. Once part or all of the gene or coding sequence is cloned, it is sequenced using conventional methods from a mutant and wild-type fish and mutations can be identified.

If no candidate genes appear to represent the mutation, a positional cloning approach will be used (FIG. 15). The first step in positional cloning is to create a fine resolution map around the region of the mutation by obtaining closely linked markers of no more than 1 cM distance from the mutation. Once these tightly linked markers have been obtained a chromosomal walk can be initiated. A mapping panel of at least 1500 diploid mutant DNAs can, for example, be utilized. The tightly linked marker is cloned and used to probe YAC, PAC and BAC libraries. The ends of these isolated clones are sequenced, tested for linkage to the mutation, and used to reprobe the libraries. Once a clone has been isolated that appears to contain the mutation, this clone can be used to probe cDNA libraries to isolate genes in this region. Alternatively, the large insert clones could be sequenced or subjected to exon trapping. Any genes isolated can be tested for the ability to rescue by injection. Also, the alleles can be sequenced to locate the mutation.

Tumor suppressors isolated can be placed on the radiation hybrid panel. Therefore, it may be possible to clone a candidate gene by co-localization of a linked marker and a mapped gene. Candidate genes may also be suggested by the synteny of the zebrafish map with the human and mouse genomes. To rule candidate genes in or out, single stranded conformational polymorphisms (SSCPs) can be used to assess linkage to the mutation.

If no known or expressed sequences are identified from the chromosomal region identified using linkage analysis or none of the ESTs result in identification of a gene that harbored the cell cycle defect causing mutation, the genes in the region can be identified using conventional cloning methods from libraries containing fish genomic DNA. A variety of methods are available for gene cloning. Principal procedures include physical mapping by construction of a large continuous DNA fragments, contigs, using YACs and BACs/PACs, P1 s, STS-content mapping, DNA fingerprinting, pulsed field gel electrophoresis, and end sequence rescue.

For example, the genetic markers that flank the chromosomal region of interest identified using linkage analysis can be used to identify a clone or clones that contain the chromosomal region in any number of different libraries such as YAC, BAC/PAC, or P1. The identification can be performed either using well known hybridization methods using the linkage analysis marker region as a probe or PCR using primers amplifying the linkage analysis marker region. Once the correct clone or clones have been identified they can be subjected to sequence analysis and the sequences from the wild-type fish can be compared to the sequence from the mutant fish.

Once a large DNA fragment containing the region of interest is identified, the large-insert DNA can either be sequenced directly or transferred into cells, ES or other cell lines using, for example, lipofection, spheroplast fusion, or pronuclear injection.

Gene identification from large cloned DNA segments is accomplished using, for example, cDNA selection and/or exon trapping. Once a gene or coding sequence is identified it can be subjected to both expression analysis using cell cultures and transgenic animal models, and computer-based analysis. The computer-based analysis can use, for example, data and applications available on the World Wide Web. These data include fish marker maps, databases and similarity analysis programs such as BLAST, and expression profile information.

After identification of the mutant gene it can be used, for example, to identify a homologue of the gene in another species, e.g. humans. The thereby identified genes are useful as diagnostic tools for analysis of human cell cycle defects such as cancer.

The genes can also be used in preparing constructs for production of specific antibodies against the peptide encoded by the gene. These antibodies can thereafter be used as diagnostic tools in identifying cell cycle defects.

One may also create an array consisting of a number of genes involved in cell cycle regulation and use the array as a diagnostic tool to simultaneously analyze problems in a variety of cell cycle regulating genes. The arrays may be used to determine a specific cell cycle defect in, e.g. a human affected with cancer, thereby allowing a more targeted treatment plan.

The newly identified genes involved in cell cycle regulation are also useful in drug screening assays and molecular modeling to identify targeted inhibitors or activators for the genes.

The methods of the invention simplify the evaluation, identification, and development of active agents for the treatment and prevention of conditions involving defective cell cycle, which may be excessive or insufficient, depending upon the condition. These screening methods provide a facile means for selecting natural product extracts or compounds of interest from a large population which are further evaluated and condensed to a few active and selective materials. Constituents of this pool are then purified and evaluated in the methods of the invention to determine their cell cycle inhibiting or cell cycle-inducing activities.

For example, compounds that modulate expression of a newly identified gene can be screened using the mutants ability to disturb cell cycle in fish. For example, the mutant fish can be subjected to a test agent such as a pharmaceutical compound or a small molecule including organic and non-organic molecules. If the tumor formation is reduced in the mutant fish exposed to the test agent, the test agent is a tumor growth inhibiting agent that is a specific inhibitor to the newly identified mutation causing a cell cycle defect.

In general, novel drugs for the treatment of conditions involving cell cycle defects are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broth, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their cell cycle inhibiting or cell cycle inducing activities should be employed whenever possible.

When a crude extract is found to have cell cycle inhibiting or cell cycle inducing activities or both, further fractionation of the positive lead extract is necessary to isolate chemical constituents responsible for the observed effect. Thus, the goal of the extraction, fractionation, and purification process is the careful characterization and identification of a chemical entity within the crude extract having cell cycle inhibiting or cell cycle inducing activities. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of cancer known in the art.

Below are described examples of screening methods for identifying and evaluating the efficacy of a compound as a cell cycle inhibiting or cell cycle inducing agent. These methods are intended to illustrate, not limit, the scope of the claimed invention.

a) Screens for Compounds Affecting Protein Expression in Fish

The newly identified DNA fragments may be used to facilitate the identification of compounds that increase or decrease their expression in fish. In one approach, candidate compounds are added, in varying concentrations, to the tank harboring mutant fish expressing the identified mRNA. The mRNA expression is then measured, for example, by Northern blot analysis [Ausubel, F. et al., Current Protocols in Molecular Biology, John Wiley & Sons, New York, 6.3.1–6.3.6, 1994] using a DNA, or cDNA or RNA fragment specific for the cell cycle component such as pH3 or the newly identified nucleic acid as a hybridization probe. The level of mRNA expression in the mutant fish in the presence of the candidate compound is compared to the level of mRNA expression in the absence of the candidate compound, all other factors (e.g., the fish growing conditions) being equal.

The effect of candidate compounds on cell cycle may, instead, be measured at the level of translation by using the general approach described above with standard protein detection techniques, such as Western blotting or immunoprecipitation with a specific antibody recognizing a cell cycle component, such as pH3 as described above, or the newly identified cell cycle regulatory protein.

Compounds that modulate cell cycle in a fish may be purified, or substantially purified, or may be one component of a mixture of compounds such as an extract or supernatant obtained from cells, from mammalian serum, or from growth medium in which mammalian cells have been cultured [Ausubel et al., supra]. In an assay of a mixture of compounds, the cell cycle regulatory protein, such as pH3, expression is tested against progressively smaller subsets of the compound pool (e.g., produced by standard purification techniques such as HPLC or FPLC) until a single compound or minimal number of effective compounds is demonstrated to modulate cell cycle regulation.

Compounds may also be screened for their ability to modulate cell cycle regulation in the mutant fish. For example, one can measure the apoptosis inducing activity using the methods described above. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the cell cycle regulating activity in the fish is to screen for compounds that interact physically with a given polypeptide, the novel protein identified using positional cloning methods described above. These compounds are detected by adapting, for example, yeast two-hybrid expression systems known in the art. These systems detect protein interactions using a transcriptional activation assay and are generally described by Gyuris et al. [*Cell* 75:791–803, 1993] and Field et al. [*Nature* 340:245–246, 1989], and are commercially available from Clontech (Palo Alto, Calif.). In addition, U.S. Pat. No. 5,702,897 describes a yeast two-hybrid assay in which proteins involved in apoptosis, by virtue of their interaction with BCL-2, were detected. A similar method can be used to identify proteins and other compounds that interacted with cell cycle regulating proteins.

A compound that increases the expression or biological activity of the cell cycle regulating protein in a fish is considered useful because such a molecule may be used, for example, as a therapeutic to increase cellular levels of the protein. Such compounds could be used to correct cell cycle defects that result from decreased or absent activity of a tumor suppressor gene, i.e. gene that serves to protect an organism from tumor formation. Such tumor suppressor genes include, but are not limited to, retinoblastoma, $p21^{WAF1}$, $p27^{KIP1}$ and $p16^{Ink-4a}$ A compound that decreases cell cycle regulating protein activity (e.g., by decreasing gene expression or biological activity) may also be used to increase cellular proliferation. This would be advantageous in the treatment of cancers caused by oncogenes directly affecting cell proliferation such as ERBB, RET, SRC, RAS, ABL, MYC or JUN.

(b) Modifier Screens

The suppressor screen is used to identify genes that modify the pH3 expression levels in the mutant fish. These suppressors may modify the rate of cancer formation in the carcinogenesis assay. Alternatively, the suppressor may alter the quality or tissue-specificity of the tumor biology. In mouse knockout models of tumor suppressor genes, some mutants live to adulthood; whereas others represent embryonic lethal defects. For instance, mice deficient in p53 or pl6INK4 are viable; whereas the NF-1, PTEN, RB, and BRCA1 knockout mice are lethal during embryogenesis. Mice deficient in mismatch repair genes (such as the msh) genes are mostly viable [Ghebranious, N., Oncogene, 17:3385–3400, 1990]. Thus, it is difficult to predict whether the zebrafish mutants isolated here will be viable or lethal during embryogenesis. Homozygous viable mutants are subjected to dominant suppressor screens. Mutants that are not viable as homozygotes, a recessive enhancer-suppressor screens are carried out to evaluate genes that, when mutant, "cure" the cancer. These genes are excellent pharmaceutical targets for patients with cell cycle proliferation defects such as patients with cancer or leukemia.

The availability of cell cycle mutants in the zebrafish allows the isolation of novel tumor suppressor genes involved in cancer. Using these mutants, it is possible to do dominant suppressor screens or suppressor-enhancer screens to evaluate gene interactions and pathways. Based on the way the screens are performed, each mutant displays abnormal expression of, for example, pH3. Using the carcinogenesis assay, particular mutants with increased or decreased cell proliferation indicated, for example by increased or decreased pH3 staining will be identified. These mutants are likely to be prone to cancer. In the suppressor screen, genes that modify, for example, the pH3 expression levels in these mutants can be identified. These suppressor genes may also modify the rate of cancer formation in the carcinogenesis assay.

Figure 16A:
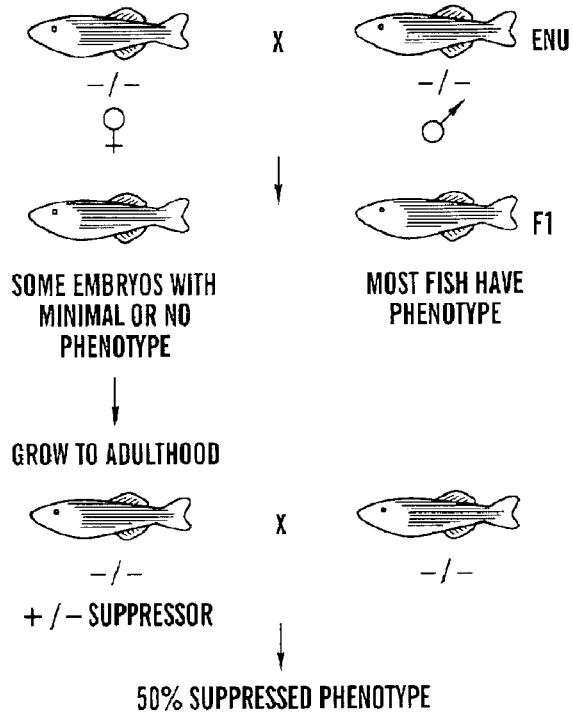
FIGS. 16(A)–(B) is an illustration of modifier screens using fish model.

FIG. 16(A) shows a dominant suppressor screens for viable mutants. Homozygous viable mutant males were treated with ENU. This causes point mutations to occur in the spermatogonia and the male is mated to a female homozygous mutant. Most resulting embryos will have abnormal pH3 staining and alterations in cell death. Apoptosis markers as described above or a phenotypic characteristic (such as the tail-up phenotype) are used to examine suppressors. Newly derived mutants that lack apoptosis based on, for example, the viable dye lysotracker red or acridine orange are evaluated further. These mutants are grown to adulthood and then back-crossed to their parents to demonstrate a dominant suppression of the cell cycle phenotype. Once this dominant suppressor is available, the gene can be cloned using positional cloning methods. Carcinogenesis assay can be used to demonstrate that the identified suppressor gene dominantly suppresses the cancer phenotype.

FIG. 16 shows a scheme for modifier screens of the original phenotypes. FIG. 16(A) is an outline of dominant suppressor screen. Previously identified homozygous viable mutant males are exposed to ENU mutagenesis thereby inducing point mutations. These males are then bred to homozygous mutant females. The majority of the F1 clutches from these matings recapitulate the original phenotype. However, if the ENU induced mutations occur in modifier genes of the original phenotype, the original mutant's phenotype is suppressed. These fish are raised to adulthood and subsequently backcrossed to their parents to demonstrate 50% suppression of the original phenotype in the F2 clutch.

If no mutants are viable as homozygotes, but heterozygotes are prone to cancer formation, an enhancer-suppressor screen or a recessive enhancer-suppressor screens can be performed.

For example, ENU-mutagenized males are mated to heterozygous females. Progeny that is heterozygous and carrying secondary mutations is identified by random mating. A haploid screen is performed using these fish, and screening for, for example pH3 at, about 36 hrs. These are examined for suppressors or enhancers (for example, 25% of mutants will change in pH3 staining). Identified suppressing mutations are mapped and cloned. The new mutants interacts with the previously derived cell cycle mutant genes, functioning as a suppressor of the tumor phenotype.

Figure 16B:
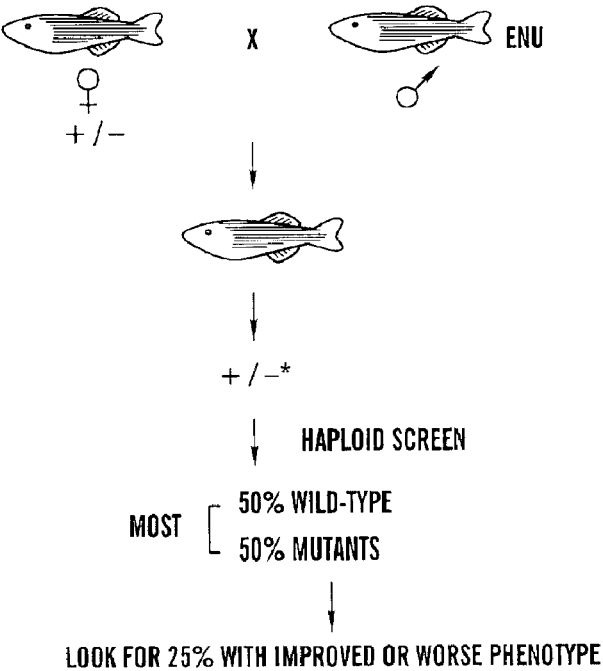
Figure 17A:
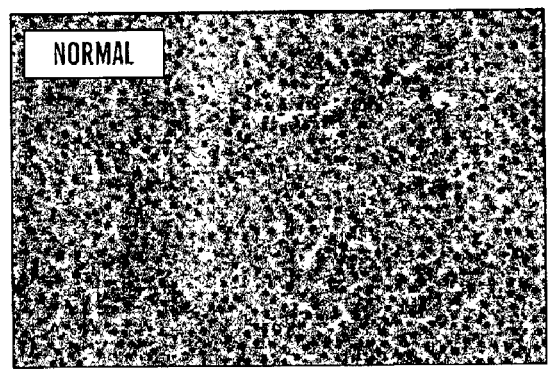
FIGS. 17(A)–(C) show normal and tumor histology of the liver. The tumor is marked by arrows in 17(B). The histology is consistent with a hepatocellular carcinoma.
Figure 17B:
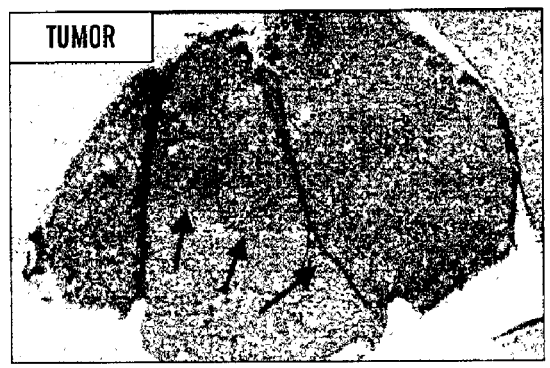
Figure 17C:
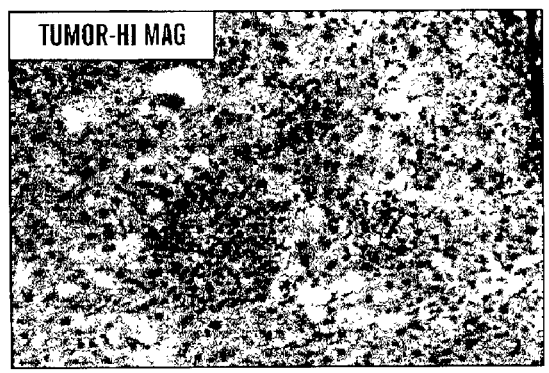

FIG. 16(B) is an outline of recessive enhancer-suppressor screen. Heterozygous females (for the original mutation) and wild-type ENU-treated males are mated together. F1 females heterozygous for the initial mutation are identified by tail-clipping. These fish are doubly heterozygous by virtue of the second ENU mutation from the father. A haploid screen is then performed with two possible outcomes. If the second mutation does not modify the original mutation, the clutch would be 50% wild type and 50% mutant. On the other hand, if the second mutation did modify the original phenotype, 25% of the clutch would show either an enhanced or suppressed phenotype.

The power of the dominant suppressor screen is that many genes can be studied, completely saturating the genome for interacting genes. However, these dominant mutations may be dominant negatives or haplo-insufficient genes. Another advantage of the dominant suppressor screen is that several mutants can be studied since these screens are relatively quick.

Molecules that are identified, by the methods described above, to effectively modulate cell cycle activity in a fish may be tested further in other animal models. If they continue to function successfully in an in vivo setting, they may be used as therapeutics to either inhibit or enhance cell cycle, as appropriate.

Figure 12:
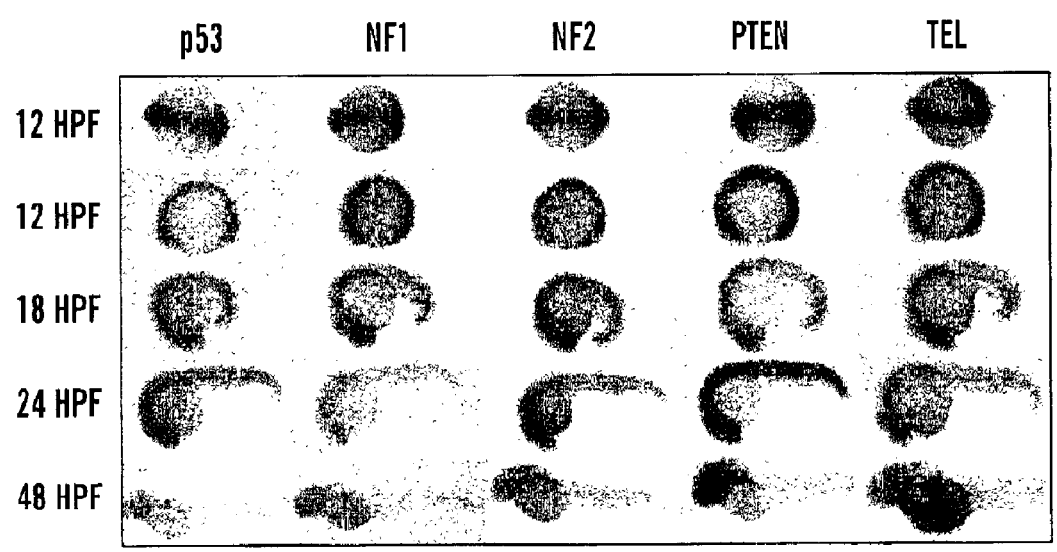
FIG. 12 is an in situ hybridization of zebrafish embryos showing expression of the tumor suppressor genes p53, Nf1, Nf2, PTEN/MMAC1 and the oncogene Tel during the first 48 hours of embryonic development.

For example, tumor suppressor genes in mouse, human and *Drosophila* have provided information about the molecular basis of cancer and growth regulation. In addition, targeted disruptions and overexpression studies have also supplied invaluable information about the role of these genes. We have already isolated several zebrafish homologues of known tumor suppressor genes (FIG. 11(A)–(B)). The cloned tumor suppressor genes include RB, NF-1, NF-2, LATS, APC, and PTEN/MMAC2, as well as several oncogenes including myc and ras. In situ hybridization studies for gene expression provide invaluable information when it comes to cloning the mutant genes, providing candidates for the mutant genes. FIG. 12 shows an in situ hybridization demonstrating embryonic expression of the tumor-suppressor genes p53, Nf1, Nf2 and PTEN/MMAC1 and the oncogene Tel during the first 48 hours of development. While in general the genes are ubiquitously expressed, there are tissue-specific differences such as expression of p53 in the ICM at 24 hpf, heavy expression of Nf2 and PTEN in the developing brain, and somite-specific expression of PTEN at 12 hpf.

Figure 13A:
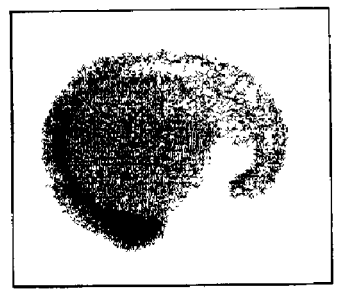
FIGS. 13(A)–(C) are an in situ hybridization of zebrafish embryos showing expression of AS-7 compared to phospho-histone H3 staining in SQW 213 mutant. (A) 18 somites; (B) 24 hours; and (C) SQW 213 mutant.
Figure 13B:
Figure 13C:
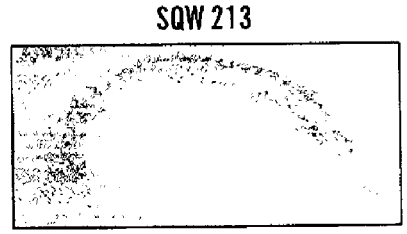

In a whole embryo in situ hybridization screen of over 4000 independent cDNA clones, over 50 genes were found to be expressed in a similar domain as pH3 staining (FIG. 13(A)). The sequences of these cDNAs largely consisted of genes involved in the cell cycle. Eighteen of these represent the zebrafish orthologs of human ESTs of unknown function or novel genes. The expression of these cDNAs can be used to characterize the cell cycle in wild-type and mutant embryos. Interestingly, the domain of cDNA AS7 is very similar to the pH3 staining seen in mutant SQW 213 (FIG. 13(B)–(C)), particularly staining neural cells and the pronephric duct. These genes can be positioned on a fish radiation hybrid map, and thus provide candidates for the mutant genes.

EXAMPLES

ENU Mutagenesis Adult male zebrafish of the wik-background were mutagenized with ENU and mated to wild-type females of the same background. The ENU mutagenesis was performed essentially as described in van Eeden et al. [*Methods Cell Biol* 60: 21–41, 1999]. Shortly, male zebrafish are exposed to about 2.5–3.0 mM ENU in Embryo medium for one hour at 25° C. Fish are washed to two changes of fish aquarium water for one hour each wash. The treatment can be repeated about 3 and 6 days later. After exposure to mutagens, male fish are mated weekly to wild-type female fish. The F1 progeny generated 4–24 weeks after the last ENU treatment are used for screening.

Creation of Haploid Embryos

The F1 heterozygote females harboring point mutations created using ENU mutagenesis described above were squeezed to produce haploid eggs that were fertilized with UV inactivated sperm, yielding haploid embryos.

The F1 female fish were placed in isolation chambers with a male fish overnight. The next morning, prior to egg laying, the males were removed. The females were individually anesthetized with 0.02% Tricahe, and their eggs were removed by gentle pressure on the abdomen. The eggs were mixed with 2.0 microfilters of VU-inactivated sperm. After one minute embryo water was added. The embryos were subsequently incubated at 28.5° C.

Whole Mount Immunohistochemical Staining of Zebrafish Embryos

The haploid embryos were screened at 36 hours with an anti-phospho histone H3 antibody to screen for potential cell cycle mutants. Clutches were analyzed under a stereo dissecting microscope and scored for an abnormal number of stained cells in 50% of the embryos. The parental F1 females from those clutches with 50% abnormally staining embryos were set aside.

750 F1 female zebrafish were screened resulting in identification of 41 mutant clutches: 21 had increased staining, 11 had decreased staining and 9 had other phenotypes, such as focal staining.

There are several alternative fixation methods that can be used before staining. Here, the embryos were fixed 4 hours in 4% paraformaldehyde. After fixation, the embryos were stained with an antibody recognizing the phosphorylated histone H3 (pH3).

The staining was performed using a peroxidase method. The embryos were fixed and stored in 5 ml glass vials. The embryos were first dechlorinate using watchmaker forceps or pronase treatment. Pronase treatment is faster for large batches of embryos. To dechlorinate the embryos using pronase, 2 mg of pronase was added on them in E3 medium. The preparation was swirled at room temperature until about 80% of the chorions were removed after which the preparation was rinsed 3–4 times with E3.

Embryos were fixed with 4% paraformaldehyde/PBS overnight at 4° C. and consequently washed twice in PBS.

Staining with antibody was performed by first incubating the fixed embryos for 7 minutes in −20° C. acetone in glass vials. The embryos were rinsed once in double distilled water and twice in PBS for one minute in each after which they were washed 2 times 5 minutes in PBS with 0.1% Tween-20 (PBST).

Unspecific binding was blocked by incubating embryos for 30 minutes to one hour at room temperature with PBST and blocking reagents (10% heat treated lamb serum, 2% blocking reagent diluted from a 10% stock (Boehringer-Mannheim Biochemicals (Roche)) and 1% DMSO.

Primary anti phospho histone H3 antibody was diluted to 1 ug/ml in PBST/block reagents/DMSO and incubated overnight at 4° C. or at room temperature for 2–4 hours. Primary antibody was removed and the preparation washed 4 times 15 minutes in PBST. Secondary anti-rabbit IgG antibody conjugated to horse radish peroxidase (HRP; Jackson Immunoresearch) at 1:300 in PBST/block reagents/DMSO was added to the embryo preparation and incubated overnight at 4° C. or room temperature for 4 hr.

Detection of staining was performed after rinsing once and then washing for 30 minutes with PBST and 10% heat treated lamb serum and three times 30 minutes in PBST. The DAB stain was added at appropriate dilution and stained for 10 minutes to overnight wrapped in foil to protect from light. Often a staining time of 1 to 5 minutes was adequate. After staining the preparation was washed two times 5 minutes in PBST and fixed in 4% paraformaldehyde/PBS overnight at 4° C. The stained preparations were stored in fixative at 4° C. or alternatively in methanol. The preparations were mounted in 90% glycerol, 10% 1×PBS and photographed. Alternatively, the preparation can be dehydrated and mounted. Dehydration can be performed with washing with 100% MetOH twice, 10 minutes each, followed by a 2:1 mixture of benzylbenzoate:benzylalcohol wash. This mixture has the same refractive index as yolk, and clears the embryos well but it is not viscous like glycerol and embryos are hard to position.

Histone H3 phosphorylation has long been implicated in chromosome condensation during mitosis [Strahl, B. D., et al., Nature, 403:41–45, 2000]. Phosphorylation at Ser10 of histone H3 is tightly correlated with chromosome condensation during both mitosis and meiosis (Hendzel et al. Chromosome 106:348–360, 1997). Phosphorylation at this site is also required for the initiation of the chromosome condensed state, as well as the induction of immediate-early genes such as c-jun, c-fos and c-myc [Strahl, B. D., et al., Nature, 403:41–45, 2000], [Spencer, V. A., et al., Gene, 240:1–12, 1999]. PKA, Rsk-2 and MSK1 are required for H3 phosphorylation [Strahl, B. D., et al., Nature, 403:41–45, 2000], [Spencer, V. A., et al., Gene, 240:1–12, 1999]. Phospho-Histone (Ser10) Antibody detects Histone H3 when it is phosphorylated at serine 10. It is a useful tool to identify the phosphorylation of H3 and monitor cell mitosis and meiosis by immunocytochemistry.

The pH3 antibody stains cells known to be proliferating in zebrafish embryos. Stained cells were distributed throughout the embryo at 12 and 16 hours post fertilization (hpf) and increased in number from 24–48 hpf. As each organ undergoes proliferation during distinct developmental stages, pH3 staining increases. There was a particularly high concentration of staining in the eye and developing nervous system 24–48 hpf (FIG. 2(A)–(D)). High magnification views of these stained embryos showed many mitotic figures demonstrate that pH3 antibody stains cells undergoing mitosis (FIG. 3(A)). The stained cells in the eye were different from cells in the lens that undergo apoptosis (FIG. 3(B)). Staining of later stage embryos has proven unsuccessful, although it is unclear whether this is a result of a decrease in pH3 levels or a decrease in the permeability of the embryo to the pH3 antibody.

Staining performed on haploid embryos also delineated mitotic cells. To demonstrate the specificity of pH3 antibody for cycling cells, we tested pH3 staining in embryos that were irradiated (FIG. 4). Irradiation induces a checkpoint after which cells subsequently begin to cycle. After irradiation, pH3 staining decreased to a nadir at 30 minutes, and recovers to near normal levels by 2 hours.

Whole Mount In Situ Analysis of Zebrafish Embryos The whole mount in situ analysis was performed essentially as described by S. Schulte-Merker, J. H. Odenthal, and C. N üsslein-Volhard The Zebrafish Science Monitor. 2, Sep. 21, 1992 at zfish.uoregon.edu/zf_info/monitor/vol2.1/vol2.1.html].

The embryos were dechorionated using watchmaker forceps or pronase treatment and fixed with 4% paraformaldehyde/PBS overnight at 4° C. as described above. The dechorionated embryos were washed 2 times in PBS for 5 minutes at room temperature. The washed embryos were transferred to vials with 100% methanol and incubated for 5 minutes. Methanol was replaced with fresh 100% methanol and put at −20° C. for at least 20 minutes.

The dechorionated embryos were rehydrated and fixed at room temperature. Embryos were processed in batches according to age (proteinase K treatment) and later separated. Either 5 ml vials or 12 well plates. Each wash was 2 to 3 ml in the vials or 50 ml in the well trays: 5 minutes in 50% MetOH in PBST, 5 minutes in 30% MetOH in PBST and 2 times in PBST, 5 minutes each (dechorionating embryos can also be done at this point, but chorions are sticky after having been in MeOH). The rehydrated embryos were fixed for 20 minutes in 4% paraformaldehyde in PBS and washed with 2 times PBST (PBS, 0.1% Tween) for 5 minutes each.

The dechorionated preparations were digested with proteinase K (10 µg/ml in PBST) at room temperature for about 5 minutes (time can vary from 1 minute up to 10 hours), 10 minutes (10–24 hours) or 15 minutes (20 µg/ml in PBST) (>24 hours). After digestion, the preparations were rinsed briefly in PBST; washed once in PBST for 5 minutes and fixed as described above; and washed again two times in PBST as described above.

Up to 200 embryos were transferred into 1.5 ml microfuge tubes in PBST. PBST was removed so that the embryos are just covered and add approximately 500 µg HYB⁻ solution (50% formamide, 5×SSC, 0.1% Tween-20). Hybridization steps were performed in a water bath or preferably in a hybridization oven without rocking. The preparation was allowed to incubate 5 minutes at 60° C. whereafter HYB⁻ was replaced by an equal volume of HYB+ (HYB⁻, 5 mg/ml torula (yeast) RNA, 50 µg/ml heparin). Prehybridization was performed at 60° C. for 4 hours in HYB+(overnight prehybridization was sometimes preferred). About 5 to 10 µg of a linearized plasmid was used and probes shorter than 2500 nucleotides were not hydrolyzed.

Hybridization was performed by adding 100 ng RNA probe to 500 µl fresh HYB+ and heated for 5 minutes at 68° C. The probe in HYB+ was added and the preparation was incubated overnight or about 12 hours at 60° C. whereafter the probe was removed.

The following GATA-2 and TTG2 steps were performed on 24 well plates using prewarmed solutions.

GATA-2 probe was the most common starting point. The following incubations were performed: 2×30 minutes at 60° C. in 50% formamide/2×SSCT (SSC, 0.1% Tween); 1×15 minutes at 60° C. in 2×SSCT; and 2×30 minutes at 60° C. in 0.2×SSCT.

TTG2 probe was used to decrease background. The following incubations were performed: 30 minutes at 60° C.

in 50% formamide/50% 2×SSCT; 3×10 minutes at 37° C. in 2×SSCT; 1×5 minutes at 37° C. in PBST; 30 minutes at 37° C. in RNAse A, 20 µg/ml, RNAse T1, 100U/ml in PBST solution; 10 minutes at 37° C. in 2×SSCT; 60 minutes at 60° C. 50% formamide/50% 2×SSCT; 15 minutes at 60° C. 2×SSCT; and 2×15 minutes at 50° C. in 0.2×SSCT.

The detection of staining was performed as follows. The embryo preparation was washed 2×5 minutes in MABT (100 mM maleic acid (Sigma M0375, St Louis, Mo.), 150 mM NaCl, 55 g tris for 2L final, pH 7.5 combined with 0.1% Tween-20). The preparation was blocked for one hour at room temperature with MABT plus blocking reagents (10% heat treated lamb serum, 2% BMB 1096 176 (Boehringer-Mannheim Biochemicals, Indianapolis, Ind.), blocking reagent in 100 mM maleic acid (Sigma M0375), 150 mM NaCl, 55 g tris for 2L final, pH 7.5). Fab-AP as supplied by Boehringer was added at a 5000-fold dilution and shaken overnight at 40° C. in MABT plus blocking reagents.

The preparation was rinsed once then wash 30 minutes with MABT and 10% heat treated lamb serum and once again with 5×30 minutes in MABT. Embryos were washed 3×5 minutes in staining buffer 100 mM Tris, pH 9.5, 50 mM $MgCl_2$, 100 mM NaCl, 0.1% Tween-20, 1 mM Levamisole. Embryos were stained at room temperature in BMB purple (Boehringer-Mannheim Biochemicals) and 5 mM fresh levamisole hydrochloride for 30 minutes to overnight. Embryos were washed two times for 5 minutes in PBST and fixed overnight and stored in 4% paraformaldehyde/PBST at 4° C. For photography, the embryos were placed in 70% glycerol 30% 1×PBST.

Flow Cytometric Cell Sorting Analysis of Zebrafish Embryos to Identify Defects in cell Cycle To analyze the DNA content of the embryos wild-type and mutant embryonic cells were subjected to DNA flow cytometric cell sorting (FACS). FIG. 7(A) shows that FACS analysis of DNA content can be performed on cells from a single embryo allowing analysis and comparison of mutant and wild-type cell cycle phenotypes.

Embryos were anesthetized with tricaine (3-amino benzoic acid ethylester also called ethyl m-aminobenzoate, in a powdered form from Sigma, Cat.# A-5040). Tricaine solution for anesthetizing fish was prepared by combining the following: 400 mg tricaine powder, 97.9 ml DD water, and about 2.1 ml 1 M Tris (pH 9), pH was adjusted to about 7. Before use 4.2 ml of Tricaine solution was mixed with 100 ml clean tank water.

The embryos were dechorionated as described above and resuspended in a small volume of DMEM–20% FBS in a microtube. Embryos were disaggregated and resuspend in 1–2 ml of DMEM+20% FBS. The solution was passed through 105 µm mesh, and consequently 40 µm mesh. The total volume was raised to 5 ml and the cells in the sample was counted using hemocytometer. Volume equaling $2×10^6$ cells was transferred in 15 ml conical tube and filled to a total volume of 5 ml with PBS. The sample was spinned at 1200 rpm for 10 minutes and the liquid was aspirated off. 2 ml PI solution (0.1% Sodium Citrate, 0.05 mg/ml propidium iodide, 0.0002% Triton X100 and 2 µg of RNase was added. The sample was incubated in dark at room temperature for 30 minutes before transferring on ice and sorting on a FACS analyzer.

Gamma radiation induced a cell cycle arrest in zebrafish embryos as seen by DNA content analysis by FACS. Cell cycle arrest in early G2 produced both the increase in cells with 4N DNA content and the decrease in the number of mitotic cells. FIG. 7. (B) shows that flow cytometric analysis of 24 hours post fertilization zebrafish embryos demonstrated accumulation of cells in G2-phase, indicating activation of the G2 DNA-damage checkpoint. Consistent with the known kinetics of eukaryotic DNA repair, reversal of G2 arrest was seen beginning at 2 hrs post-radiation. During this same time period, pH3 immunoreactivity was profoundly depressed, suggesting that the G2 radiation checkpoint preceded the onset of chromatin condensation and H3 phosphorylation.

The analysis of SQW226 (FIG. 7(C)) and SQW 280 (not shown) demonstrated endoreduplication (arrow), a feature commonly found in human tumors such as neuroblastoma, suggesting that the increased pH3 staining in whole mount truly indicated an increase of cells at the G2/M boundary in vivo. The DNA content analysis of mutants SQW 226, SQW 319, and SQW 61 demonstrated aberrant cell cycles including the following characteristics: endoreduplication (extra peak) (SQW 226), populations of larger cells (SQW 226 and SQW 61), an increase in the G2/M population (SQW 319), and an increase in the G1population (SQW 61). Decrease of G2 and increase in G1 population in SQW61 analysis suggested that the cells were arrested in G1 stage.

Analysis of Apoptosis Markers in Zebrafish Embryos to Identify Defects in Apoptosis Embryos were stained for 1 hr in acridine orange, washed in PBS and observed with fluorescein filter.

Apoptosis in zebrafish embryos can be detected using a variety of techniques. For example, acridine orange staining of SQW 226 demonstrated that the mutant has a significant increase in cell death at 24 or 36 hrs. Cells with defective cell cycle undergo an apoptotic death. FIG. 8 shows that mutant SQW 226 demonstrated an increased number of cell undergoing cell death as compared with the wild-type. Heterozygous in-crosses of SQW 226 were performed. At 24 hours, it was apparent that one quarter of the clutch displays a "tail up" phenotype. These homozygous embryos were then stained with the vital dye acridine orange and examined under an epifluorescent microscope to evaluate the extent of apoptosis.

Lysotracker (Molecular Probes, Eugine, Oreg.) is an aldehyde fixable red dye that also stains apoptotic cells in live embryos, and allowed us to further study the mutants in conjunction with other probes. FIGS. 21(A)–(F) demonstrate a significantly increased apoptosis in various zebrafish embryo mutants using Acridine Orange staining.

BrdU Staining of Zebrafish Embryos to Identify Defects in S phase

BrdU is incorporated into DNA by cells in S phase. The BrdU assay allowed further refinement of the cell cycle phenotype. FIG. 9(B) shows BrdU labeling of wild-type and mutant zebrafish embryos and a time course of BrdU labeling in wild-type zebrafish embryos.

Live 24 hours post fertilization embryos were incubated in 10 mM BrdU on ice, rinsed and chased for 0, 10, 30 and 60 minutes at 28.5° C. Details of labeling in the eye and tail demonstrated a progressive increase in labeled cells with longer incubations.

Analysis of SQW 226 and 319 zebrafish mutants is shown in FIG. 8(C). Both mutants demonstrated decreased incorporation of BrdU. BrdU incorporation in wild-type and mutant embryos after a 10-minute chase period showed that S-phase cells are moderately decreased in SQW226 and severely decreased SQW 319. FIGS. 20(A)–(F) demonstrates BrdU staining of zebrafish embryos 36 hours post fertilization and the defective staining is clearly seen in mutants SQW 226 (20(D)) and SQW 319 (20(F)).

Summary of analysis of zebrafish mutants using pH3 staining, apoptosis markers, BrdU incorporation and FACS is shown in the following Table I.

TABLE I

Characterization of SQW mutants. n.d.= not determined.; ↑ = increased number of cell staining; ↓ = decreased staining.

| Mutant | H3 staining | Apoptosis | BrdU incorp. | DNA flow |
|---|---|---|---|---|
| 61 | ↓ posteriorly | n.d. | ↓ | Increased cells in G1 |
| 213 | ↑ neural/ pronephric duct | ↑ | n.d. | Normal |
| 226 | ↑↑↑ | ↑↑ | ↓ | Polyploid |
| 280 | Large spots | n.d. | n.d. | Polyploid |
| 319 | ↓↓↓ | ↑ | ↓↓ | Increased cells in G2 |
| 332 | ↓↓ | n.d. | ↓↓ | n.d. |
| 333 | ↑ | n.d. | n.d. | n.d. |

Tubulin Staining of Zebrafish Embryos to Identify Defects in Mitosis

The mitotic spindle plays a vital role in cell cycle, and the mutants could represent defects in this process. Tubulin staining of the zebrafish for examining mitosis was performed Disrupted zebrafish embryos were incubated on polylysine coated slides and air dried. The slides were incubated in PBST/Block (as described above) followed by incubation in fluorescein conjugated monoclonal anti-α-tubulin (Sigma) diluted 1:100 and washed in PBST. The slides were observed under microscope with a fluorescein filter. FIGS. 19(A)–(F) demonstrate defective spindle formation in two mutants, SQW 280 in 19(B)–(C) and SQW 226 in 19(D)–(E).

Irradiation Analysis of Zebrafish Embryos to Identify Checkpoint Defective Mutant Zebrafish embryos were γ-irradiated 24–36 hours post fertilization with 800–1600 rads which causes a cell cycle arrest (FIG. 4), yet the embryo recovers and continues to develop normally at least about to 24 hours of age. pH3 staining decreases substantially to being barely detectable by 30 minutes post radiation, but pH3 recovers to normal levels at 2 hours post radiation. DNA flow cytometric analysis demonstrates an increasing proportion of cells in G2/M from 15 minutes post radiation to 4 hours post radiation, suggesting a G2 arrest.

Eggs from 100 F1 females harboring mutations were squeezed and exposed to inactive sperm to create haploid embryos. The embryos were evaluated at 12 hours and irradiated at 14 hours with 1600 rads. One hour later the embryos were fixed as described above and stained for pH3. One mutant, R176 showed 50% mutant embryos with persistent pH3 staining suggesting a damaged radiation checkpoint.

We irradiated SQW 226 to evaluate whether SQW 226 mutant zebrafish strain has checkpoint defects. SQW 226 mutant zebrafish did not show a decrease in the number of mitotic cells as the homozygous mutants fail to display decreased pH3 staining shown in FIG. 9. Therefore, either SQW226 is able to override a checkpoint or alternatively exhibits an exit block which suggests that either SQW 226 is resistant to the radiation-induced cell cycle arrest or the cell cycle is blocked and shows no effect from radiation. In contrast, wild-type embryos (+/− or +/+) had decreased pH3 staining after irradiation. Each mutant was evaluated in this irradiation screen for cell cycle checkpoint defects.

In addition, this irradiation screen forms the basis for doing a checkpoint or exit block screen on zebrafish embryos. FIG. 10 shows that a haploid screen that was performed based on the observed radiation-induced cell cycle arrest. Haploid embryos from F1 females, which is the progeny of ENU treated males and wild-type females, was irradiated and fixed 45 minutes post radiation. These embryos were stained with the pH3 antibody and mutants that did not exhibit the normal decrease in mitotic cells can be identified. These mutants are likely to affect cell cycle machinery or checkpoint control genes and are excellent models for the study of cancer formation and as subjects for future modifier screens.

Creation and Analysis of Diploid Embryos

The 41 F1 wik-ENU female zebrafish representing the potential mutations were outcrossed to wik males. The resulting F2 progeny was raised to adulthood and in-crossed to re-identify heterozygote pairs and to confirm that the pH3 phenotype can be recapitulated in the diploid state.

Figure 5A:
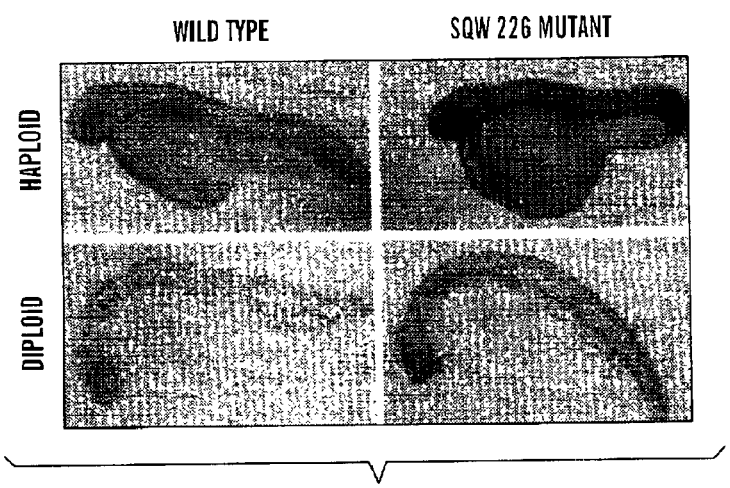
FIGS. 5(A)–(F) are a presentation of a whole-mount immunohistochemical staining using phospho-histone H3 antibody in wild-type and mutant zebrafish embryos. It demonstrates an example of mutant zebrafish strains with a variety of defects in the cell cycle that can be observed using a cell cycle specific antibody phospho-histone H3. (A) A comparison between haploid (top panel) and diploid (bottom panel) wild-type (left panel) and SQW 226 mutant (right panel) phenotypes. (B) SQW 226 mutant embryo (bottom) shows globally increased cell proliferation compared to a wild-type embryo. (C) SQW 213 mutant embryo (bottom) shows increased cell proliferation along the neural axis as well as a focal increase in the terminal pronephric duct (arrow) compared to a wild-type embryo (top). (D) SQW 319 mutant embryo (bottom) shows globally decreased cell proliferation compared to a wild-type embryo (top). (E) SQW 61 mutant embryo (bottom) shows decreased cell proliferation in the trunk and tail compared to a wild-type embryo (top). (F) SQW 280 mutant embryo (bottom) shows altered size of nuclei and/or cells compared to a wild-type embryo (top).
Figure 5B:
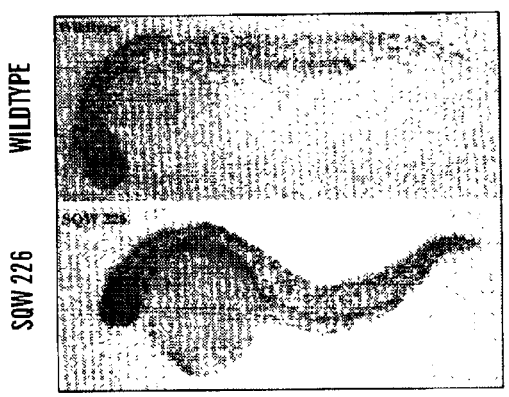
Figure 5C:
Figure 5D:
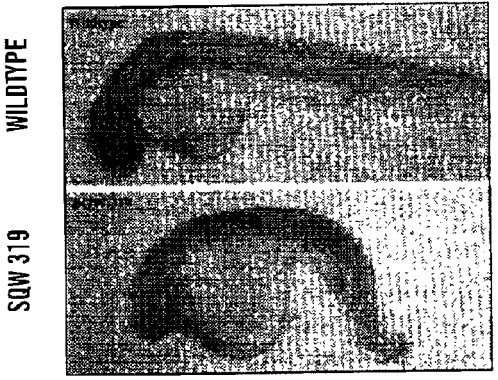
Figure 5E:
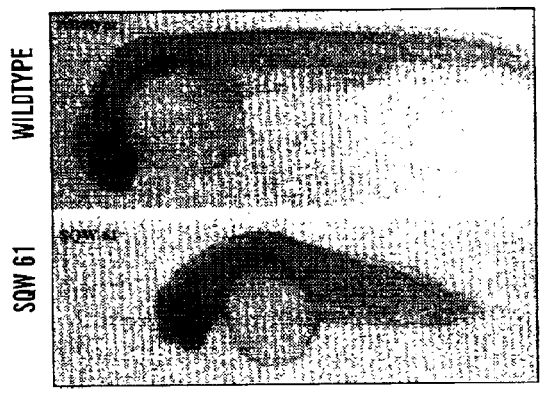
Figure 5F:
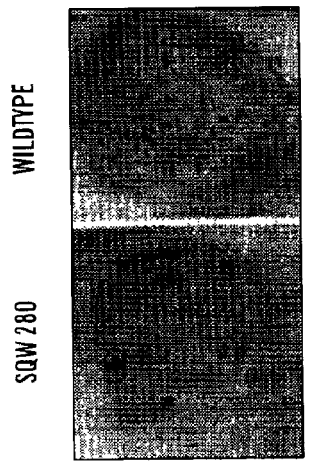

We identified the progeny from 29 F 1 females that have been in-crossed (20 matings each). In this analysis, heterozygote pairs for seven mutations (SQW 61, 213, 226, 280, 319, 332, 333) were identified. FIG. 3 shows the analysis of several mutants. The SQW 226 mutant had increased pH3 staining. Counting cells in the body and tail (n=5) demonstrated 2.2 fold more stained cells in the mutant compared to wild-type. The diploid phenotypes for these mutants resembled the haploid phenotypes (FIG. 5(A) and 5(B)). SQW 213 also had increased staining but in a focal distribution in neural cells and in the pronephric duct (FIG. 5(C)). SQW 319 has decreased pH3 staining (FIG. 5(D)), and SQW 61 had only slightly increased staining (FIG. 5(E)); SQW 280 had a larger domain of nuclear staining with fewer cells staining (FIG. 5(F)). Map crosses for all 41 F1 females (wik.ENU heterozygous female crossed to a wild-type AB male) were also generated.

Given average mutant recovery rates from haploid screens that we performed, the pilot screen will recover at least 15–20 mutants affecting the cell cycle. In some mutants, there was an increase in pH3 staining diffusely. In these mutants, there was a decrease in the size of the head and a curved up tail. Other mutants had decreased pH3 staining and appeared smaller than control siblings.

Positional Cloning of Genes Involved in Cell Cycle Regulation a. Linkage analysis.

The mutants were mapped onto zebrafish linkage groups by either determining centromeric linkage by half-tetrad analysis [Johnson, S. L., et al. *Genetics*, 139:1727–1735, 1995] or by scanning microsatellites for linkage. This half tetrad method involved following the segregation of known SSLP centromeric markers with respect to wild-type and mutant gynogenetic diploid embryos [Streisinger, G., et al., *Nature*, 291:293–296, 1981; Streisinger G., et al., *Genetics*, 112:311–319, 1986].

The mutation can also be assigned to a linkage group, by bulk segregation analysis with CA repeat markers [Talbot W. et al., in *Methods in Cell Biology* eds. H. I. Detrich, M. Westerfield, L. Zon, Academic Press, San Diego: 260–284, 1999; Liao, E. et al. Id. at 181–183]. A wik background fish carrying the mutation (heterozygote) is mated to a polymorphic strain (AB). Haploid embryos are generated from heterozygous wik/AB hybrid females by fertilizing eggs with UV-irradiated sperm. Alternatively, diploid embryos can be generated by mating heterozygous hybrid males and females. Either haploid or diploid embryos are scored as either wild-type or mutant by fixing and staining them with the anti-pH3 antibody. DNA is then made from individual embryos. Bulk segregation analysis is performed on wild-type and mutant pools of 20 DNA samples (two wild-type pools and two mutant pools) (FIG. 11A). PCR will then be performed on these pools using CA repeat primers from the linkage group indicated. Bands that amplify from both AB and wik DNA are uninformative; however, bands that are polymorphic between the two strains can be used as positional markers. A linked marker will be identified as one that segregates in the pools, meaning that bands of different sizes are amplified from the wild-type as compared to the mutant pool. If a linked marker is found, it will be tested on individual embryos to determine the recombination frequency between the marker and the mutation.

Using this approach, we genotyped 600 mutant embryos and mapped SQW226 to chromosome 11 of the zebrafish. A marker within 1.2 cM of the mutation was isolated (8/612 embryos). Because there are only 3000 CA markers currently available it may be necessary to screen other markers because a closely flanking marker may not be found. AFLP analysis has proved to be a useful way to test many markers simultaneously. Testing 256 primer combinations can yield information on 6400 loci [Ghebranious N., et al., *Oncogene*, 173385–3400, 1990].

Using linkage analysis, the following six mutants were located in zebrafish genome map: SQW 61 was mapped on chromosome 2; SQW 213 was mapped on chromosome 8; SQW 226 was mapped to chromosome 11; SQW 280 was mapped to chromosome 6; SQW 319 was mapped to chromosome 13; and SQW 333 was mapped to chromosome 15. Mutants SQW 61 and SQW 213 are flanked with markers that can be analyzed on an agarose gel example of which is shown in FIG. 14.

1664 mutant embryos for SQW226 mutant zebrafish strain were collected and the ESTs in the critical interval were tested for recombination using linkage analysis. Six recombinants were obtained out of the 1664 mutant embryo DNAs that were tested. The recombinant fish are used for a chromosomal walk to identify the SQW 226 gene. [Talbot and Schier, *Methods Cell Biol* 60:260–287, 1999].

Cloning of unknown genes is performed from libraries including BACs, PCAs, or YACs as described, for example in Amemiya et al. [*Methods Cell Biol* 60: 236–259, 1999]. Mutation detection, nucleic acid sequencing and sequence analysis can be performed using techniques well known in the art and described in detain in for example *Molecular Cloning: A Laboratory Manual*. Third Edition By Joe Sambrook, Peter MacCallum, David Russell, CSHL Press, 2001]

Carcinogenesis Assay

Carcinogenesis assay is used to determine which mutants are relevant to development of tumors or cancer. The assay will show whether zebrafish mutants that have abnormal cell cycle according to the haploid embryo screening described above are more prone to developing cancer than their wild-type siblings. The carcinogen should accelerate tumor development in these fish.

Both mutant and wild-type 3-week-old fish are exposed to the carcinogens 7, 12 Dimethyl benzanthracene (DMBA) at doses of about 1.0, 2.0, 5 and 10 ppm and N-methyl-N-nitro-N-nitrosoguanidine (MNNG) at doses of about 0.5, 1.0, 2.0 and 3.0 ppm for an approximately 24-hour period and then placed into fresh water and raised to adulthood. Survival of the fish is monitored and fish that die or look ill are fixed for sectioning. Alternatively, an entire cohort can be fixed for sectioning and histologic analysis of tissues at an arbitrary time point which is usually about 7 months.

Carcinogen-treated zebrafish develop, for example, medulloblastoma or germ cell tumors that closely resembles human disease as shown in FIG. 4. Wild-type fish were with DMBA and MNNG. 9/86 or 10.4% fish treated with DMBA developed tumors and 10/128 or 7.8% of the fish treated with MNNG developed tumors. DMBA resulted in more brain and liver tumors whereas MNNG yielded more mesenchymal and testicular tumors. Mung: 0.5, 1.0 and 2.0 ppm; DMBA: 2.5, 5.0 and 10.0 ppm.

To evaluate rates of spontaneous and carcinogen induced tumorigenesis in mutant strains, the 21 day-old fry from incrosses were exposed for 24 hours to either vehicle control (DMSO) or 5.0 ppm DMBA. The early death rate observed in the mutants resulted in analyzing the fish at 3 months rather than 6 months which was originally estimated as appropriate. Several of the mutants show an increase in tumor incidence compared to the wild-type as can be seen in the Table II below.

TABLE II

Summary of the results form the carcinogenesis assay.
n.d. = not determined; * Wild-type data are from
6 months post-treatment. The mutant strains were
analyzed three months post-treatment.

| Genotype | DMSO | | | DMBA | | |
|---|---|---|---|---|---|---|
| | # tumors | # treated | % | # tumors | # treated | % |
| WT* | 0 | 35 | 0 | 2 | 39 | 5 |
| SQW 61 | 0 | 16 | 0 | 24 | 132 | 18 |
| SQW 213 | 1 | 64 | 2 | 2 | 28 | 7 |
| SQW 226 | 0 | 61 | 0 | 4 | 20 | 20 |
| SQW 280 | 1 | 43 | 2 | 6 | 47 | 12 |
| SQW 319 | 1 | 10 | 10 | n.d. | — | — |
| SQW 333 | 2 | 31 | 6 | n.d. | — | — |

Figure 6A:
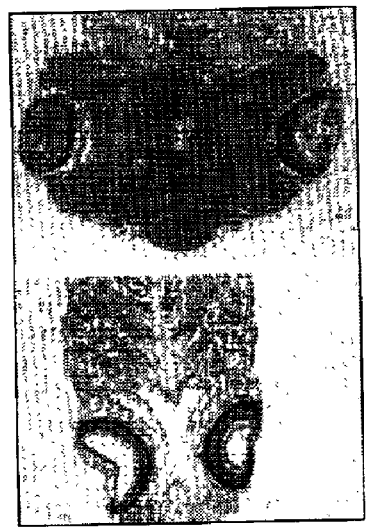
FIGS. 6(A)–(E) show an analysis of zebrafish tissue sections after the carcinogenesis assay using histological and computer assisted methods. The histological staining shows a striking histological similarity of a variety of tumors in zebrafish and human. The computer analysis demonstrates the decreased lifespan of mutant zebrafish exposed to a carcinogen. (A) Tissue sections from a medulloblastoma induced by dimethylbentzanthracene. Top: a zebrafish treated with dimethylbentzanthracene. Bottom: wild-type zebrafish. (B) Medium resolution view of tumors showing similarity between zebrafish (top) and human (bottom). (C) A high resolution view of tumors showing similarity between zebrafish (left) and human (right). (D) A tissue section of a germ cell tumor in a zebrafish treated with N-methyl-n'-nitrosoguanidine, low power resolution (left), high power resolution (right). (E) Kaplan-Meyer survival curve prepared using WinStat software. Comparison of life span of a control and MNNG-treated (2 ppm) zebrafish, n=40 for each group.
Figure 6B:
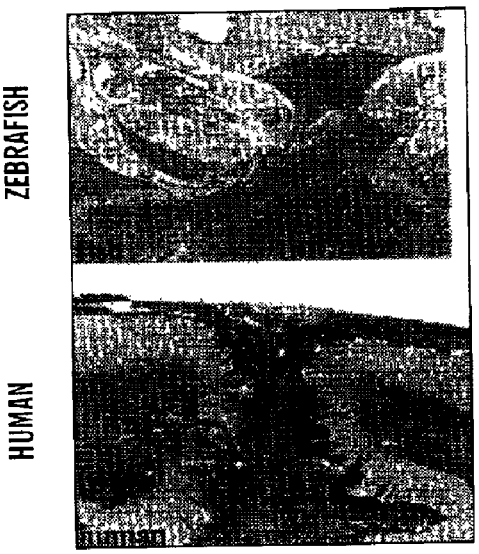
Figure 6C:
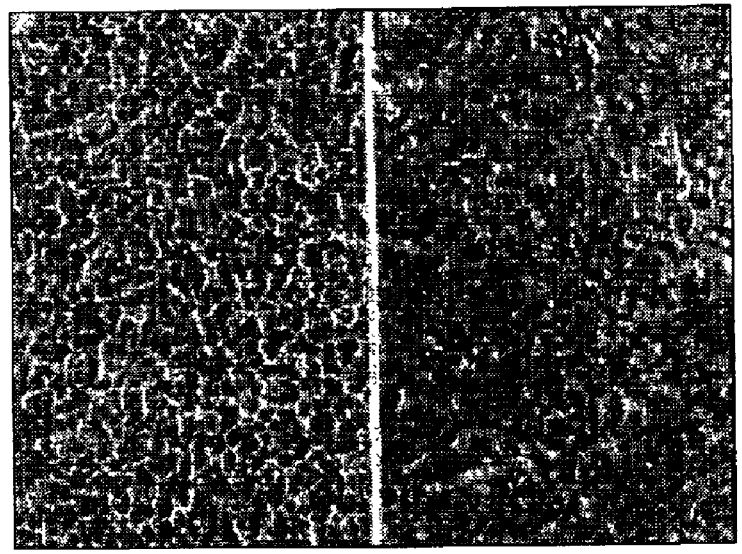
Figure 6D:
Figure 18A:
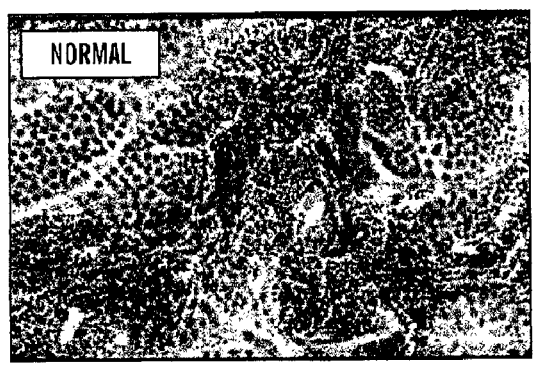
FIGS. 18(A)–(C) show normal and tumor histology of testis. The testis tumor has very large dysplastic cells (arrowhead), although some spermatocytic differentiation occurs.
Figure 18B:
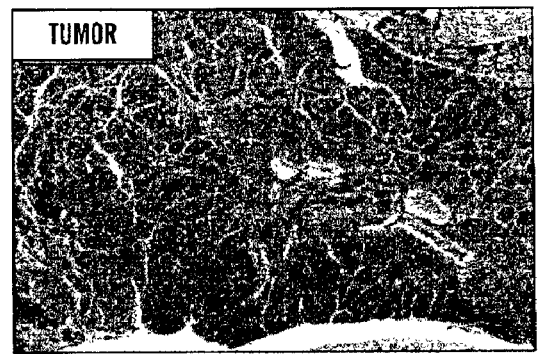
Figure 18C:
Figure 19A:
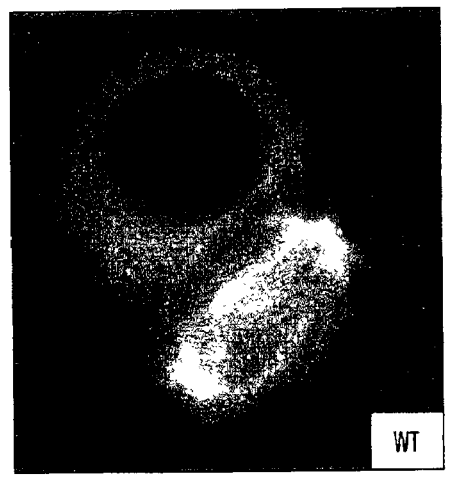
FIGS. 19(A)–(E) show alpha-tubulin staining of zebrafish embryos and demonstrate aberrant spindle formation in mutant embryos.
Figure 19B:
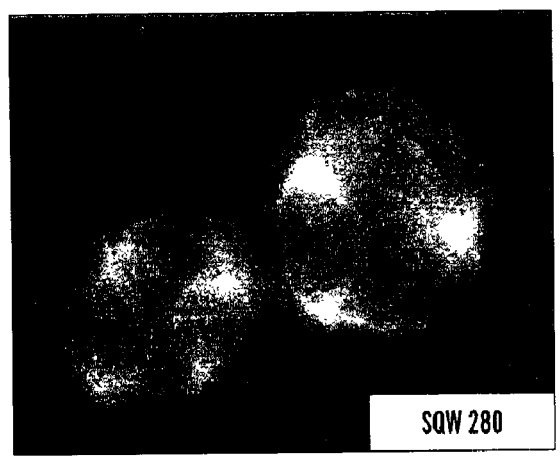
Figure 19C:
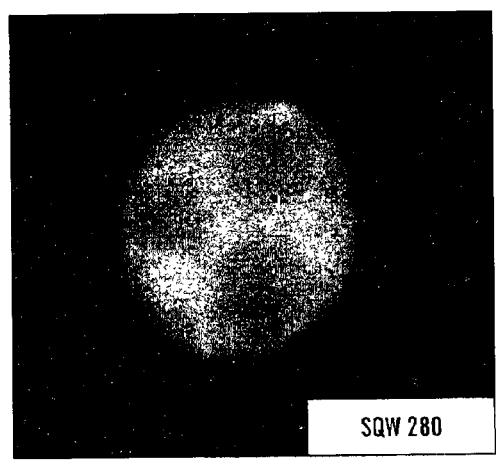
Figure 19D:
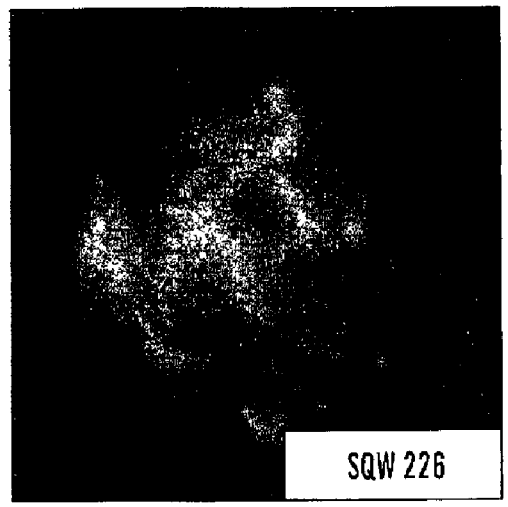
Figure 19E:
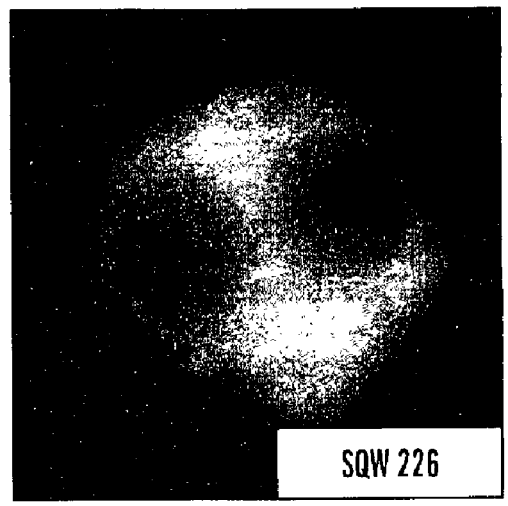
Figure 20A:
FIGS. 20(A)–(F) show BrdU incorporation in 36 hours post fertilization embryos.
Figure 20B:
Figure 20C:
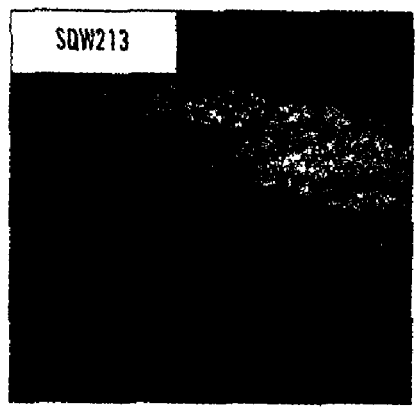
Figure 20D:
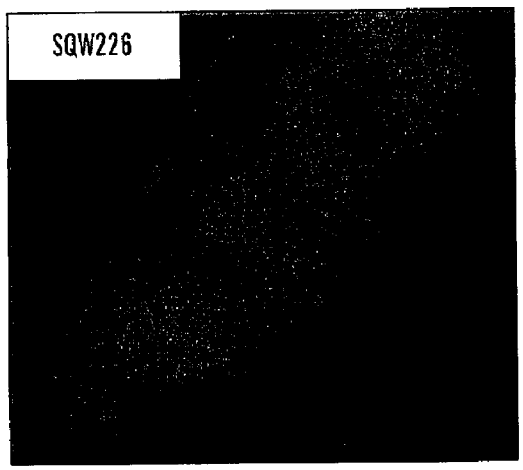
Figure 20E:
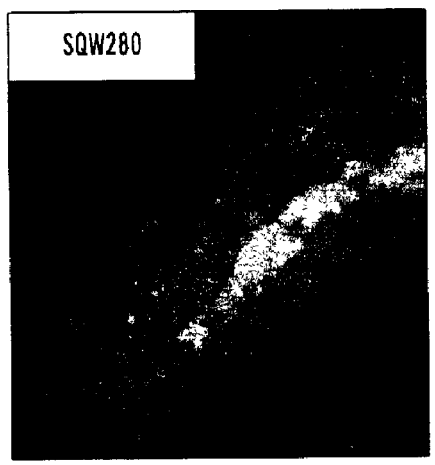
Figure 20F:
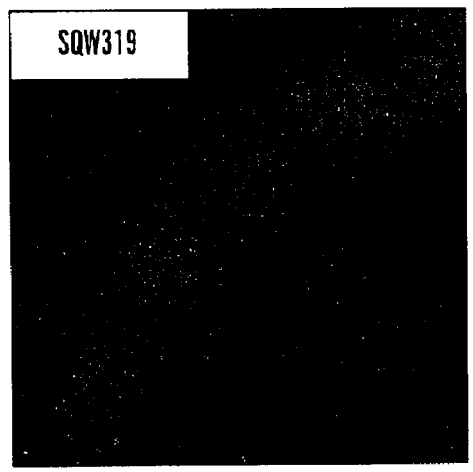
Figure 21A:
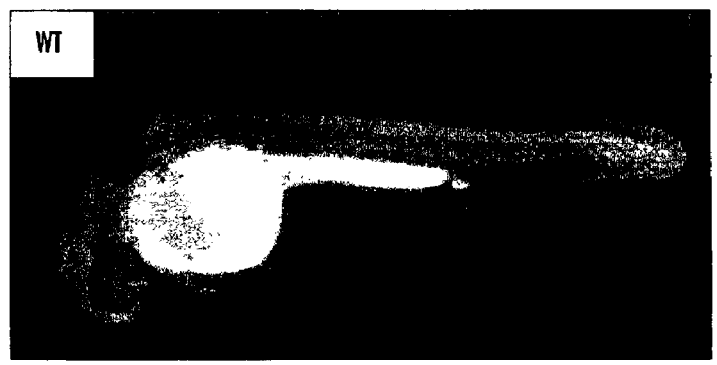
FIGS. 21(A)–(F) demonstrates excess apoptosis in mutant zebrafish embryos.
Figure 21B:
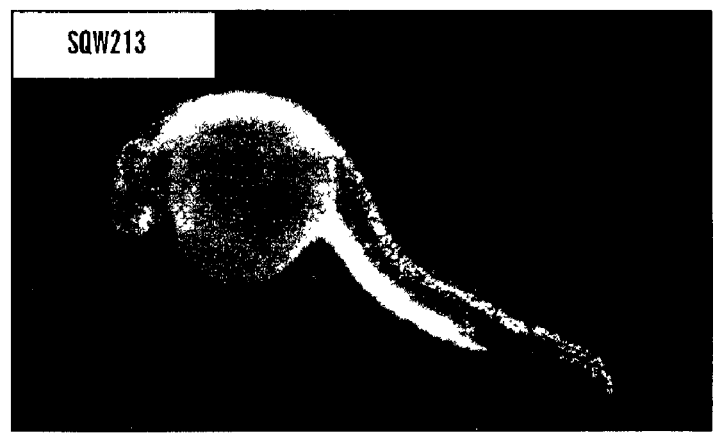
Figure 21C:
Figure 21D:
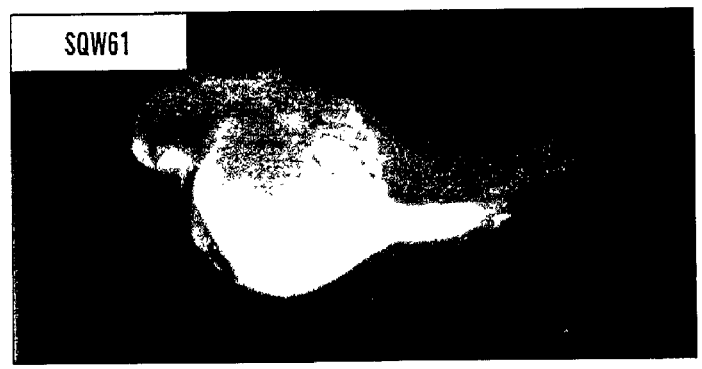
Figure 21E:
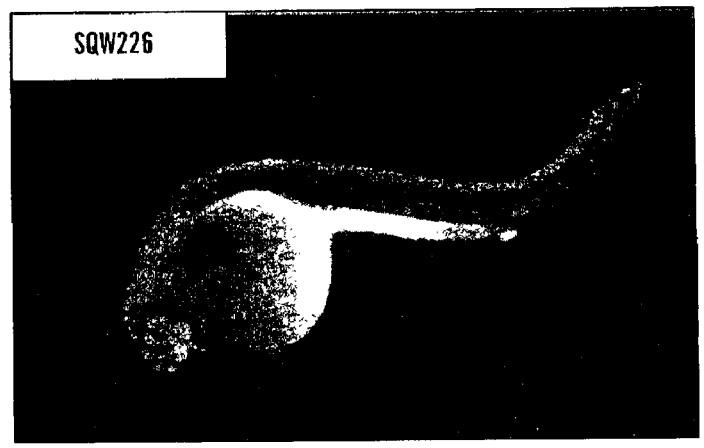
Figure 21F:
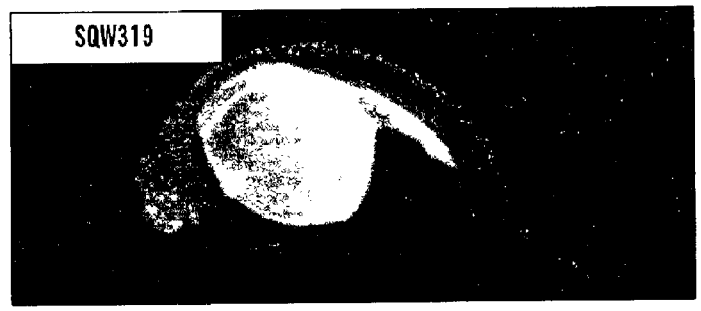

FIG. 6(A) shows tissue sections from a medulloblastoma in a fish treated with (7,12) dimethylbenzanthracene on the top compared to wild-type on the bottom using low power view. Low resolution indicates 40×, medium 200× and high 400× magnification. A medium FIG. 6(B) and high FIG. 6(C) resolution views show the similarity of fish and human tumors. FIG. 6(D) shows a low-resolution (left) and high-resolution (right) views of a germ-cell tumor in a fish treated with N-methyl-N'-nitrosoguanidine. FIGS. 17(A)–(C) and 18(A)–(C) illustrate liver and testis tumors, respectively. The arrow in FIG. 17(B) indicates the liver tumor in 100× magnification and 17(C) shows a 400× magnification of the same tumor. Control liver sample is shown on FIG. 17(A). In FIG. 18(B) the testicular tumor is shown in 100× magnification and in FIG. 18(C) the same tumor is shown in 400× magnification. The arrowhead indicates the large, dysplastic cells present in the tumor sample. FIG. 18(A) shows a control testis sample.

Figure 6E:
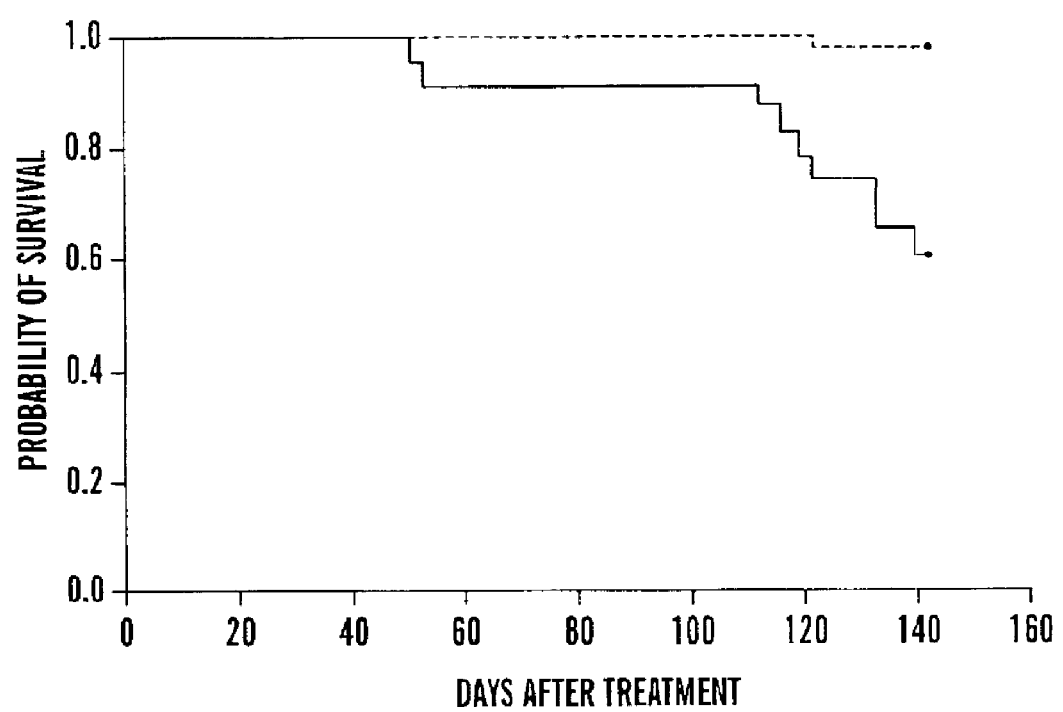

Tumorigenesis and death in the clutch will be studied by Kaplan-Meier statistical analysis. FIG. 6(E) shows a Kaplan-Meier survival curve that was produced using WinStat software program comparing the lifespan of control and MNNG-treated zebrafish (using MNNG concentration of 2 ppm). The number of fish in each group was 40 (n=40). Genotyping of the progeny will be performed to confirm linkage of cancer phenotype to the mutant gene.

The homozygous mutants that are prone to getting cancer can consequently be subjected to dominant suppressor screens. Alternatively, mutants that are heterozygous and prone to cancer can be subjected to enhancer-suppressor screens for recessive mutants.

All the references cited above in the specification are hereby incorporated by reference in their entirety.

It will be apparent to those skilled in the art that various modifications and variations can be made to the present invention without departing form the spirit and scope of the invention. Thus, it is intended that the present invention cover the modifications and variations provided they come within the scope of the appended claims and their equivalents.

We claim:

1. A method of identifying a fish with a gene mutation involved in carcinogenesis comprising the steps of:
   (a) exposing a fish to a mutagen;
   (b) mating said fish from step (a) with a wild-type fish to produce an F1 generation;
   (c) exposing haploid eggs derived from a female fish of said F1 generation to inactivated fish sperm to create haploid embryos; and
   (d) screening said haploid embryos for cell proliferation defects wherein an embryo with cell proliferation defects is determined to harbor a gene mutation involved in cell proliferation;
   (e) mating an F1 generation female harboring the gene mutation involved in cell proliferation as determined in step (d) with a wild-type fish to produce an F2 generation;
   (f) exposing a wild-type fish and a member of the F2 generation to a carcinogen; and
   (g) comparing the tumor formation in the wild-type and the member of the F2 generation fish wherein an accelerated tumor formation in the F2 generation fish identifies the fish with the gene mutation that is involved in carcinogenesis.

2. The method of claim 1, wherein the fish is a zebrafish.

3. A method of identifying a fish gene involved in carcinogenesis, wherein the method comprises the step of:
   (a). Providing a F2 generation fish with a gene mutation as identified in step (g) of claim 1;
   (b). isolating the mutant gene involved in carcinogenesis by positional cloning.

4. The method of claim 1, wherein the screening is performed using an antibody against a cell cycle component.

5. The method of claim 4, wherein the antibody is specific for a protein selected from the croup consisting of phospho-histone H3, phosphorylated MAP kinase, phosphorylated MEK-1, BM28, cyclin E, p53, Rb and PCNA.

6. The method of claim 1, wherein the screening is performed using nucleic acids recognizing cell cycle components.

7. The method of claim 6, wherein the nucleic acid is PCNA or cyclin b-1.

8. The method of claim 1, wherein the screening is performed using flow cytometry wherein DNA in the haploid embryos is stained with a dye and separated according to their DNA content using flow cytometry wherein changes in the DNA content indicate a problem in cell proliferation.

9. The method of claim 1, wherein the screening is performed using apoptosis markers.

10. The method of claim 9, wherein the apoptosis marker is selected from the group consisting of Annexin V, TUNEL Stain, 7-amino-actinomycin D and Caspase substrates.

11. The method of claim 1, wherein the screening is preformed using BrdU staining.

12. The method of claim 1, wherein the screening is performed using an irradiation analysis comprising the steps of irradiating the mutated embryos to cause a cell cycle arrest, staining the embryos with a cell proliferation marker and analyzing the amount of the marker post radiation wherein change in the post radiation marker staining compared to an irradiated non-mutant embryos indicates an abnormal cell proliferation in the mutant embryo.

* * * * *

SEQUENCE LISTING

<160> NUMBER OF SEQ ID NOS: 3

<210> SEQ ID NO 1
<211> LENGTH: 903
<212> TYPE: PRT
<213> ORGANISM: Danio rerio

<400> SEQUENCE: 1

```
Met Pro Pro Lys Lys Arg Ser Ser Gly Thr Pro Gln Lys Lys Glu Leu
1               5                   10                  15

Lys Gly Ser Leu Lys Ser Arg Ser Pro Asp Ser Gly Asp Asn Ala Val
            20                  25                  30

Leu Ser Pro Glu Arg His Lys Asp Lys Asp Pro Glu Phe Val Phe Leu
        35                  40                  45

Ser Glu Glu Leu Gln Ser Thr Asn Ser Ile Cys Asp His Ala Trp Arg
    50                  55                  60

Ile Trp Glu Arg Glu Ile Arg Ser Met Asp Lys Thr Asn Met Pro Tyr
65                  70                  75                  80

Ser Asn Arg Gln Gln Trp Gly Ala Cys Leu Phe Ile Ala Gly Met Glu
                85                  90                  95

Leu Glu Gly Ile Asn Leu Thr Phe Thr Gln Phe Leu Lys Ala Val Gly
            100                 105                 110

Leu Ser Val Lys Gln Phe Ile Ser Leu Val Arg Lys Met Asp Val Asn
        115                 120                 125

Val Asp Thr Ile Ser Pro Lys Val Asn Ser Ala Val Thr Arg Leu Glu
    130                 135                 140

Asn Lys Tyr Asp Val Thr Leu Ala Leu Tyr Gln Arg Phe Val Lys Thr
145                 150                 155                 160

Cys Glu Lys Ile Phe Ala Glu Pro Asp Asn Ala Lys Arg Lys Glu Leu
                165                 170                 175

Trp Glu Ser Ser Trp Thr Met Phe Leu Leu Ala Lys Gly Thr Phe Leu
            180                 185                 190

Gln Met Glu Asp Asp Leu Val Ile Ser Phe Gln Leu Leu Leu Cys Val
        195                 200                 205

Leu Glu Phe Phe Ala Lys Arg Leu Ser Pro Ser Leu Leu Gln Ser Pro
    210                 215                 220

Tyr Asn Ser Val Val Ser Ser Thr Leu Ser Pro Pro Thr Arg Thr
225                 230                 235                 240

Ser Arg Arg Asn Gln Gly Lys Ser Lys Pro Arg Pro Ala Glu Met Asp
                245                 250                 255

Met Gln Leu Leu Glu Thr Leu Cys Lys Glu Gly Asp Cys Ser Val Asp
            260                 265                 270

Glu Val Lys Asn Val Tyr Gln Ser Thr Phe Cys Ala Phe Leu Asp Ser
        275                 280                 285

Val Gly Leu Leu Gly Leu Gln Gly Leu Pro Pro Met Glu Ala Leu Ser
    290                 295                 300
```

-continued

```
Lys Gln Tyr Glu Glu Leu Tyr His Lys Ser Lys Asp Phe Asp Ala Arg
305                 310                 315                 320

Leu Phe Leu Ser Asp Asp Glu Thr Leu Ser Pro Asn Lys Ile Glu Val
            325                 330                 335

Ser Lys Val Glu Val Thr Pro Arg Lys Asn Leu Phe Ala Glu Asp Ile
            340                 345                 350

Ala Ile Pro Val Pro Gln Thr Pro Ile Arg Ala Ala Met Thr Ser Ile
            355                 360                 365

Gln Gln Leu Arg Gly Asp Leu Thr Ser Gly Ser Asp Gln Pro Ser Ser
        370                 375                 380

Asn Leu Leu Val Tyr Tyr Lys Asn Cys Thr Val Asp Pro Ser Gly Glu
385                 390                 395                 400

Ile Lys Lys Arg Val Glu Glu Leu Gly Glu Val Phe Ile Gln Arg Phe
                405                 410                 415

Ala Gln Ala Val Gly Gln His Cys Glu Gly Leu Gly Arg Lys Arg Phe
            420                 425                 430

Tyr Leu Gly Ala Gln Leu Tyr Tyr Lys Val Met Glu Ser Met Leu Lys
        435                 440                 445

Ser Glu Glu Lys Arg Leu Ser Val Gln Asn Phe Ser Lys Leu Leu Asn
450                 455                 460

Asn Ala Ala Phe His Thr Ser Leu Leu Ala Cys Ala Leu Glu Val Val
465                 470                 475                 480

Ile Ala Thr Tyr Val Gly Ser Ser Leu Lys Asn Gly Gly Phe Gly Arg
                485                 490                 495

Ser Ser Gly Ala Ser Asp Ser Val Glu Ser Asp Leu Cys Phe Pro Trp
            500                 505                 510

Ile Leu Ser Val Phe Gln Leu Pro Ala Phe Asp Phe Tyr Lys Val Ile
            515                 520                 525

Glu Ser Phe Ile Lys Ala Glu Pro Thr Leu Lys His Asp Met Val Lys
530                 535                 540

His Leu Glu Gln Cys Glu His Val Ile Met Glu Ser Leu Ala Trp Arg
545                 550                 555                 560

Ala Asp Ser Pro Leu Phe Asp Leu Leu Lys Gln Ser Arg Glu Glu Gly
                565                 570                 575

Pro Gly Glu Gln Ala Glu Pro Ala Thr Leu Asn Gln Pro Leu His
            580                 585                 590

His Asn His Thr Ala Ala Asp Leu Tyr Leu Ser Pro Val Arg Pro Cys
        595                 600                 605

Arg Gln Pro Pro Val Met Glu Ala Glu Pro Thr Pro Gly Thr Arg
        610                 615                 620

Ala Pro Arg Ser Asn Ser Leu Ser Leu Phe Tyr Lys Lys Leu Tyr Arg
625                 630                 635                 640

Met Ala Tyr Leu Arg Leu Lys Met Leu Phe Ser Asn Leu Leu Thr Ser
                645                 650                 655

His Pro Glu Met Glu Pro Ile Ile Trp Thr Leu Leu Gln His Thr Leu
            660                 665                 670

Gln Asn Glu Tyr Glu Leu Met Arg Asp Arg His Leu Asp Gln Leu Ile
        675                 680                 685

Met Ser Ala Met Tyr Ala Ile Cys Lys Val Lys Asn Val Asp Leu Arg
        690                 695                 700

Phe Lys Thr Ile Val Thr Ala Tyr Lys Glu Leu Pro Asn Thr Asn Gln
705                 710                 715                 720

Glu Thr Phe Lys Arg Val Leu Ile Arg Glu Gly Gln Tyr Asp Ser Ile
```

-continued

```
                725                 730                 735
Ile Val Phe Tyr Asn Leu Val Phe Met Gln Lys Leu Lys Thr Asn Ile
            740                 745                 750

Leu Gln Tyr Ser Ser Pro Arg Pro Pro Leu Ser Pro Ile Pro His
            755                 760                 765

Ile Pro Cys Ser Pro Tyr Lys Asn Ser Pro Leu Arg Val Pro Gly Ser
        770                 775                 780

Asn Asn Val Tyr Val Ser Pro Leu Lys Ser Ser Arg Val Ser Pro Leu
785                 790                 795                 800

Val Met Thr Pro Arg Ser Arg Ile Leu Ile Ser Ile Gly Glu Ser Phe
                805                 810                 815

Gly Ser Ala Asp Lys Phe Gln Lys Ile Asn Gln Met Val Ser Ser Ser
            820                 825                 830

Asp Trp Ser Leu Lys Arg Ser Leu Asp Gly Gly Ser Ala Pro Lys Pro
        835                 840                 845

Leu Lys Arg Leu Arg Phe Asp Met Asp Gly Gln Asp Glu Ala Asp Gly
    850                 855                 860

Ser Lys Ser Ser Gly Glu Ser Ala Leu Ile Gln Lys Leu Ala Glu Met
865                 870                 875                 880

Ser Ser Thr Arg Ser Arg Met Gln Glu Gln Lys Leu Lys Glu Ser
                885                 890                 895

Asp Lys Asp His Pro Glu Pro
            900

<210> SEQ ID NO 2
<211> LENGTH: 899
<212> TYPE: PRT
<213> ORGANISM: Xenopus

<400> SEQUENCE: 2

Met Pro Pro Lys Ser Pro Arg Lys Gln Gln Ile Arg Ser Gln Gly Glu
1               5                   10                  15

Pro Arg Ser Pro Asp Arg Pro Asp Phe Gln Asp Pro Asp Phe Asn Phe
            20                  25                  30

Leu Cys Glu Asn Leu Lys Ile Ser Asp Asn Val Arg Gly Lys Ala Trp
        35                  40                  45

Asn Thr Tyr Glu Lys Met Phe Pro Ser Gly Tyr Met Met Arg Glu Thr
    50                  55                  60

Ala Lys Lys Lys Glu Ser Leu Gly Leu Cys Leu Tyr Ile Ala Ser Val
65                  70                  75                  80

Asp Cys Glu Glu Met Thr Phe Thr Phe Thr Glu Leu Leu Lys Ile Leu
                85                  90                  95

Arg Leu Ser Val Asn Arg Cys Phe Arg Leu Leu Arg Glu Met Asp Ile
            100                 105                 110

Asn Met Asp Val Leu Ser Asn Lys Val Asp Asn Ala Ile Ser Lys Leu
        115                 120                 125

Lys Lys Lys Tyr Glu Asn Met Cys Leu Leu Phe Gln Lys Phe Gln Arg
    130                 135                 140

Thr Phe Glu Leu Ile Phe Glu Glu Gln His Asn Thr Arg Ala Ala Val
145                 150                 155                 160

Asp Thr Ala Pro Ile Leu Lys Gly Thr Trp Ile Thr Phe Leu Leu Ala
                165                 170                 175

Arg Gly Lys Ile Leu Gln Met Asp Asp Glu Leu Val Ile Ser Ser Gln
            180                 185                 190
```

```
Leu Leu Leu Cys Val Leu Asp Tyr Phe Ile Lys Leu Ser Pro Pro Ser
        195                 200                 205
Ile Leu Lys Glu Pro Tyr Lys Ser Ala Leu Asn Gly Leu Pro Val Asn
    210                 215                 220
Thr Pro Pro Arg Ser Ser Arg Arg Ser Gln Asn Arg Asn Thr Arg Val
225                 230                 235                 240
Ser Pro Gln Ser Glu Thr Asp Ser Lys Val Leu Glu Phe Leu Cys Ser
                245                 250                 255
Gln Asn Tyr Cys Pro Met Asp Glu Val Arg Asn Val Tyr Ser Thr Ser
            260                 265                 270
Phe Val Asp Phe Leu Ala Ser Ala Gly Ile Ser Ser Asn Glu Gly Ile
        275                 280                 285
Pro Lys Val Glu Ser Ile Ser Arg Gln Tyr Glu Glu Leu Tyr His Lys
    290                 295                 300
His Lys Asp Leu Asp Ala Arg Leu Phe Leu Glu Asn Asp Glu Thr Leu
305                 310                 315                 320
Lys Val Asp Val Gln Asp Ser Leu Asp Leu Glu Arg Thr Pro Arg Lys
                325                 330                 335
Asp Glu Ser Glu Val Phe Pro Val Pro Gln Thr Pro Val Arg Gly
            340                 345                 350
Ala Met Asn Thr Val Gln Gln Leu Met Val Thr Leu Ser Ser Ala Asn
        355                 360                 365
Asp Lys Pro Pro Asp Thr Leu Asp Ser Tyr Phe Ser Asn Cys Thr Val
    370                 375                 380
Asn Pro Lys Thr Lys Ile Thr Asp Arg Ile Glu His Phe Gly His Val
385                 390                 395                 400
Phe Lys Glu Lys Phe Ala Ser Ser Val Gly Gln Ala Cys Ala Glu Ile
                405                 410                 415
Gly Tyr Gln Arg Tyr Lys Leu Gly Val Cys Leu Tyr Tyr Arg Val Met
            420                 425                 430
Glu Ala Ile Leu Lys Thr Glu Glu Glu Arg Leu Ser Val His Asn Phe
        435                 440                 445
Ser Lys Leu Leu Asn Asn Asp Ile Phe His Ile Cys Leu Leu Ala Cys
    450                 455                 460
Ala Val Glu Val Val Ala Ser Tyr Ala Arg Asn Ala Ser Gln Ala
465                 470                 475                 480
Tyr Cys Ser Ser Gly Thr Asn Leu Ser Phe Pro Trp Ile Leu Arg Ala
                485                 490                 495
Phe Glu Ile Lys Ala Phe Asp Phe Tyr Lys Val Ile Glu Cys Phe Ile
            500                 505                 510
Lys Ala Glu Pro Ser Leu Thr Ser Asn Met Ile Lys Tyr Leu Glu Arg
        515                 520                 525
Cys Glu His Gln Ile Met Glu Cys Leu Ala Trp Gln Ser Asp Ser Pro
    530                 535                 540
Leu Phe Asp Leu Ile Lys Gln Thr Arg Glu Arg Glu Gly Leu Val Asp
545                 550                 555                 560
His Pro Glu Leu Val Ser Asn Leu Gln Gln Pro Val Gln His Asn His
                565                 570                 575
Thr Ala Ala Asp Leu Tyr Leu Ser Pro Ser Arg Ser Ser His Gln His
            580                 585                 590
Pro Val Thr Ser Val Pro Thr Ser Ser Val Thr Asn Gly Gln Val Ser
        595                 600                 605
Ser Ser Gln Pro Val Gln Gln Lys Ser Thr Ser Leu Ser Leu Phe Tyr
```

```
                610             615             620
Lys Lys Val Tyr Leu Leu Ala Tyr Lys Arg Leu Ser Ser Leu Cys Ser
625                 630                 635                 640

Ser Leu Leu Ser Asp His Pro Glu Leu Glu Gln Val Ile Trp Thr Leu
                645                 650                 655

Leu Gln His Thr Leu Gln Gln Glu Tyr Glu Leu Met Arg Asp Arg His
            660                 665                 670

Leu Asp Gln Ile Met Met Cys Ser Met Tyr Gly Ile Cys Lys Ala Lys
        675                 680                 685

Asn Ile Asp Leu Arg Phe Lys Thr Ile Val Thr Ala Tyr Lys Gly Leu
690                 695                 700

Thr Asn Thr Asn Gln Glu Thr Phe Lys His Val Leu Ile Arg Asp Gly
705                 710                 715                 720

Gln His Asp Ser Ile Ile Val Phe Tyr Asn Leu Val Phe Met Gln Lys
                725                 730                 735

Leu Lys Ser His Ile Leu Gln Tyr Gly Ser Ala Arg His Pro Thr Leu
            740                 745                 750

Ser Pro Ile Pro His Ile Pro Arg Ser Pro Tyr Arg Phe Gly Asn Ser
        755                 760                 765

Pro Lys Val Pro Gly Asn Ile Tyr Val Ser Pro Leu Lys Thr Pro Tyr
770                 775                 780

Lys Thr Ala Asp Gly Leu Leu Ser Pro Ser Lys Met Thr Pro Lys Thr
785                 790                 795                 800

Ser Phe Leu Ile Ser Leu Gly Glu Thr Phe Arg Ser Pro Asp Arg Phe
                805                 810                 815

Gln Lys Ile Asn Gln Met Leu Asn Ser Cys Glu Arg Pro Ile Lys Arg
            820                 825                 830

Ser Ala Asp Thr Gly Thr Thr Pro Lys Pro Leu Lys Lys Leu Arg Phe
        835                 840                 845

Asp Ser Asp Gly Gln Asp Glu Ala Asp Gly Ser Lys His Ile Gln Gly
850                 855                 860

Glu Ser Lys Phe Gln Gln Lys Leu Ala Glu Met Thr Ser Thr Arg Thr
865                 870                 875                 880

Arg Met Gln Lys Gln Lys Leu Glu Glu Ser Leu Glu Ser Ser Gln Gln
                885                 890                 895

Glu Glu Lys

<210> SEQ ID NO 3
<211> LENGTH: 928
<212> TYPE: PRT
<213> ORGANISM: Homo sapiens

<400> SEQUENCE: 3

Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
```

```
                    85                  90                  95
Glu Leu Trp Gly Ile Cys Ile Phe Ile Ala Arg Val Asp Leu Asp Glu
                100                 105                 110
Met Ser Phe Thr Leu Leu Ser Tyr Arg Lys Thr Tyr Glu Ile Ser Val
                115                 120                 125
His Lys Phe Asn Leu Leu Lys Glu Ile Asp Thr Ser Thr Lys Val
            130                 135                 140
Asp Asn Ala Met Ser Arg Leu Leu Lys Lys Tyr Asp Val Leu Phe Ala
145                 150                 155                 160
Leu Phe Ser Lys Leu Glu Arg Thr Cys Glu Leu Ile Tyr Leu Thr Gln
                165                 170                 175
Pro Ser Ser Ser Ile Ser Thr Glu Ile Asn Ser Ala Leu Val Leu Lys
                180                 185                 190
Val Ser Trp Ile Thr Phe Leu Leu Ala Lys Gly Glu Val Leu Gln Met
                195                 200                 205
Glu Asp Asp Leu Val Ile Ser Phe Gln Leu Met Leu Cys Val Leu Asp
                210                 215                 220
Tyr Phe Ile Lys Leu Ser Pro Pro Met Leu Leu Lys Glu Pro Tyr Lys
225                 230                 235                 240
Thr Ala Val Ile Pro Ile Asn Gly Ser Pro Arg Thr Pro Arg Arg Gly
                245                 250                 255
Gln Asn Arg Ser Ala Arg Ile Ala Lys Gln Leu Glu Asn Asp Thr Arg
                260                 265                 270
Ile Ile Glu Val Leu Cys Lys Glu His Glu Cys Asn Ile Asp Glu Val
                275                 280                 285
Lys Asn Val Tyr Phe Lys Asn Phe Ile Pro Phe Met Asn Ser Leu Gly
                290                 295                 300
Leu Val Thr Ser Asn Gly Leu Pro Glu Val Glu Asn Leu Ser Lys Arg
305                 310                 315                 320
Tyr Glu Glu Ile Tyr Leu Lys Asn Lys Asp Leu Asp Arg Arg Leu Phe
                325                 330                 335
Leu Asp His Asp Lys Thr Leu Gln Thr Asp Ser Ile Asp Ser Phe Glu
                340                 345                 350
Thr Gln Arg Thr Pro Arg Lys Ser Asn Leu Asp Glu Glu Val Asn Ile
                355                 360                 365
Ile Pro Pro His Thr Pro Val Arg Thr Val Met Asn Thr Ile Gln Gln
370                 375                 380
Leu Met Met Ile Leu Asn Ser Ala Ser Asp Gln Pro Ser Glu Asn Leu
385                 390                 395                 400
Ile Ser Tyr Phe Asn Asn Cys Thr Val Asn Pro Lys Glu Ser Ile Leu
                405                 410                 415
Lys Arg Val Lys Asp Ile Gly Tyr Ile Phe Lys Glu Lys Phe Ala Lys
                420                 425                 430
Ala Val Gly Gln Gly Cys Val Glu Ile Gly Ser Gln Arg Tyr Lys Leu
                435                 440                 445
Gly Val Arg Leu Tyr Tyr Arg Val Met Glu Ser Met Leu Lys Ser Glu
450                 455                 460
Glu Glu Arg Leu Ser Ile Gln Asn Phe Ser Lys Leu Leu Asn Asp Asn
465                 470                 475                 480
Ile Phe His Met Ser Leu Leu Ala Cys Ala Leu Glu Val Val Met Ala
                485                 490                 495
Thr Tyr Ser Arg Ser Thr Ser Gln Asn Leu Asp Ser Gly Thr Asp Leu
                500                 505                 510
```

```
Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560

Leu Ala Trp Leu Ser Asp Ser Pro Leu Phe Asp Leu Ile Lys Gln Ser
                565                 570                 575

Lys Asp Arg Glu Gly Pro Thr Asp His Leu Glu Ser Ala Cys Pro Leu
            580                 585                 590

Asn Leu Pro Leu Gln Asn Asn His Thr Ala Ala Asp Met Tyr Leu Ser
        595                 600                 605

Pro Val Arg Ser Pro Lys Lys Lys Gly Ser Thr Thr Arg Val Asn Ser
    610                 615                 620

Thr Ala Asn Ala Glu Thr Gln Ala Thr Ser Ala Phe Gln Thr Gln Lys
625                 630                 635                 640

Pro Leu Lys Ser Thr Ser Leu Ser Leu Phe Tyr Lys Lys Val Tyr Arg
                645                 650                 655

Leu Ala Tyr Leu Arg Leu Asn Thr Leu Cys Glu Arg Leu Leu Ser Glu
            660                 665                 670

His Pro Glu Leu Glu His Ile Ile Trp Thr Leu Phe Gln His Thr Leu
        675                 680                 685

Gln Asn Glu Tyr Glu Leu Met Arg Asp Arg His Leu Asp Gln Ile Met
    690                 695                 700

Met Cys Ser Met Tyr Gly Ile Cys Lys Val Lys Asn Ile Asp Leu Lys
705                 710                 715                 720

Phe Lys Ile Ile Val Thr Ala Tyr Lys Asp Leu Pro His Ala Val Gln
                725                 730                 735

Glu Thr Phe Lys Arg Val Leu Ile Lys Glu Glu Glu Tyr Asp Ser Ile
            740                 745                 750

Ile Val Phe Tyr Asn Ser Val Phe Met Gln Arg Leu Lys Thr Asn Ile
        755                 760                 765

Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
        915                 920                 925
```